US010352836B2

(12) United States Patent
Shirakami et al.

(10) Patent No.: US 10,352,836 B2
(45) Date of Patent: Jul. 16, 2019

(54) EVALUATION METHOD OF PLASTIC MATERIAL AND EVALUATION METHOD OF DEFORMATION PROCESSING OF PLASTIC MATERIAL

(71) Applicant: NIPPON STEEL & SUMITOMO METAL CORPORATION, Tokyo (JP)

(72) Inventors: Satoshi Shirakami, Yokohama (JP); Nobuo Yoshikawa, Kimitsu (JP); Tohru Yoshida, Chiba (JP); Hiroshi Yoshida, Chiba (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 260 days.

(21) Appl. No.: 15/308,680

(22) PCT Filed: May 8, 2015

(86) PCT No.: PCT/JP2015/063314
§ 371 (c)(1),
(2) Date: Nov. 3, 2016

(87) PCT Pub. No.: WO2015/170742
PCT Pub. Date: Nov. 12, 2015

(65) Prior Publication Data
US 2017/0191915 A1    Jul. 6, 2017

(30) Foreign Application Priority Data

May 8, 2014    (JP) .................................. 2014-097227
May 8, 2014    (JP) .................................. 2014-097228
May 8, 2014    (JP) .................................. 2014-097229

(51) Int. Cl.
*G01N 3/02*    (2006.01)
*G01N 3/24*    (2006.01)
(Continued)

(52) U.S. Cl.
CPC ................. *G01N 3/02* (2013.01); *G01N 3/00* (2013.01); *G01N 3/24* (2013.01); *G06F 17/5009* (2013.01);
(Continued)

(58) Field of Classification Search
CPC .................................. G01N 3/02; G01N 3/24
See application file for complete search history.

(56) References Cited

U.S. PATENT DOCUMENTS

2009/0177417 A1    7/2009    Yonemura et al.
2013/0006543 A1    1/2013    Hiwatashi et al.

FOREIGN PATENT DOCUMENTS

JP    2-31816 B2    7/1990
JP    8-16644 B2    2/1996
(Continued)

OTHER PUBLICATIONS

Choudhary et al, "Tensile stress-strain and work hardening behaviour of 316LN austenitic stainless steel", Materials Science and Technology, Feb. 2001, vol. 17. pp. 223-231.
(Continued)

*Primary Examiner* — Jamel E Williams
(74) *Attorney, Agent, or Firm* — Birch, Stewart, Kolasch & Birch, LLP

(57) ABSTRACT

An evaluation method of a plastic material includes: a first shearing process of performing simple shearing deformation with respect to a first plastic sheet; a second shearing process of performing simple shearing deformation with respect to a second plastic sheet; a first partial stress-strain curve data obtaining process of obtaining first partial stress-strain curve data; a second partial stress-strain curve data obtaining process of obtaining second partial stress-strain curve data; and a synthesized stress-strain curve data obtaining process of obtaining synthesized stress-strain curve data based on
(Continued)

the first partial stress-strain curve data and the second partial stress-strain curve data.

21 Claims, 26 Drawing Sheets

(51) Int. Cl.
  *G01N 3/00*    (2006.01)
  *G06F 17/50*   (2006.01)
  *B21D 19/08*   (2006.01)

(52) U.S. Cl.
  CPC ...... *B21D 19/08* (2013.01); *G01N 2203/0025* (2013.01); *G01N 2203/0216* (2013.01); *G01N 2203/0282* (2013.01); *G06F 2217/16* (2013.01)

(56) References Cited

FOREIGN PATENT DOCUMENTS

| | | |
|---|---|---|
| JP | 2003-154417 A | 5/2003 |
| JP | 2012-33039 A | 2/2012 |
| JP | 5131212 B2 | 1/2013 |
| JP | 2014-222160 A | 11/2014 |
| KR | 10-2008-0002410 A | 1/2008 |
| KR | 10-2008-0090551 A | 10/2008 |
| KR | 10-2012-0123724 A | 11/2012 |

OTHER PUBLICATIONS

International Search Report for PCT/JP2015/063314 dated Jul. 28, 2015.
Written Opinion of the International Searching Authority for PCT/JP2015/063314 (PCT/ISA/237) dated Jul. 28, 2015.
Yoshida et al., "Dependence of Hardening Strength on Strain Ratio (Hardening Anisotropy X) and Its Application to Assessment of Formability", Plasticity and Process, 1970, vol. 11, No. 114, pp. 513-521.
Yoshida et al., "The n and c Values Under Equibiaxial Tension and Their Applications to Assessment of Formability", Plasticity and Process, 1970, vol. 11, No. 116, pp. 670-675.
Yoshida et al., "Material models in sheet molding simulation", Plasticity and Process, 1999, vol. 40, No. 460, pp. 34-39, total 7 pages.
Korean Notice of Allowance, dated Sep. 14, 2017, for corresponding Korean Application No. 10-2016-7030313, with English translation.
Chinese Office Action and Search Report, dated Sep. 18, 2018, for Chinese Application No. 201580023772.X, with a partial English translation of the Search Report.

EVALUATION METHOD OF PLASTIC MATERIAL AND EVALUATION METHOD OF DEFORMATION PROCESSING OF PLASTIC MATERIAL

TECHNICAL FIELD OF THE INVENTION

The present invention relates to an evaluation method of a plastic material and an evaluation method of deformation processing of a plastic material.

Priority is claimed on Japanese Patent Application No. 2014-097227, filed on May 8, 2014, Japanese Patent Application No. 2014-097228, filed on May 8, 2014, and Japanese Patent Application No. 2014-097229, filed on May 8, 2014, the contents of which are incorporated herein by reference.

RELATED ART

In deformation processing of a plastic material, such as a metal material, in order to predict forming defects, such as cracks, wrinkles, springbacks, and a thickening defect; and forming conditions, such as a forming load, forming analysis which uses a finite element method is performed as described in Patent Document 1. In general, in finite element analysis, stress-strain curve data which is a material properties parameter which defines a relationship between a plastic strain and stress of the plastic material is input to a computer, and the finite element analysis is performed in the computer. In the related art, the stress-strain curve data obtained by a uniaxial tension test is approximated by a work hardening law, such as a Swift equation described in Non-Patent Document 1, and the approximated parameter of the work hardening law is input to the computer as the stress-strain curve data.

In the stress-strain curve data obtained by the uniaxial tension test, in a strain region having uniform elongation until reaching a certain tensile strength, flow stress increases as the strain increases due to the work hardening. Meanwhile, in a strain region having local elongation until a test piece fractures exceeding the tensile strength, plastic instability occurs, necking occurs in the test piece, and the flow stress deteriorates as the strain increases. In the forming analysis of press forming using finite element analysis, from the stress-strain curve data, stress-strain curve data until reaching the strain region having uniform elongation is mainly used.

In addition, according to a hydraulic bulging test described in Non-Patent Document 2 or Non-Patent Document 3, and further, according to a cylindrical upsetting test or a simple shearing test, stabilized stress-strain curve data in which unevenness is relatively small until reaching a strain region in which a uniform elongation is exceeded from a yield point, is obtained.

However, for example, in the press forming of an actual metal sheet, there is a case where a strain much greater than that of the strain region having uniform elongation is applied to a part of the metal sheet.

In addition, in the automobile field, a forming processing method which is called sheet forging is used together with press forming, cold forging, roll forming, or incremental forming (swaging or the like). Sheet forging is a technique which is a combination of press forming and cold forging. An example of sheet forging includes a method of sequentially performing a process of press forming with respect to a metal sheet in a shape of a cup by using a die and a punch, and a process of upsetting processing by pushing a tip part of the cup by another punch in a state where a bottom surface of the cup is pressed by a pad. In the method, a part which is thinned when the press forming is performed is compressed and thickened by the upsetting processing. In this manner, in the sheet forging, since cold forging is added to press forming, a strain much greater than that in the press forming is added to the metal sheet.

Therefore, in a case where forming analysis, such as press forming which uses the finite element method, sheet forging, and cold forging, is performed, by extrapolating the stress-strain curve data of the strain region having uniform elongation until reaching the strain region in which the uniform elongation is exceeded, the stress-strain curve data is approximated considering the influence of the work hardening, and the finite element analysis needs to be performed by using the approximate curve data.

As a method for extrapolating the stress-strain curve data until reaching the strain region in which the uniform elongation is exceeded, for example, there is a method for obtaining an average gradient of a stress-strain curve of the strain region having uniform elongation, and extrapolating a straight line having the average inclination until reaching the strain region in which the uniform elongation is exceeded. In addition, as another method, there is a method for obtaining a partial inclination of the stress-strain curve of the strain region having uniform elongation, and extrapolating the straight line having the inclination until reaching the strain region in which the uniform elongation is exceeded. However, even when the stress-strain curve data is extrapolated, the stress-strain curve data is approximated, and the forming analysis of the deformation processing is performed based on the approximate curve data, and in a case where accuracy of the approximate curve data is low, there is a concern that the accuracy of the forming analysis when the deformation processing is performed may deteriorate.

In addition, in the approximate curve data obtained by extrapolating the stress-strain curve data, there is a trend that an error is likely to increase as a strain amount increases. Therefore, in the forming analysis of the sheet forging or the cold forging of the related art, the approximate curve data of a high-strain region in which the error is relatively large needs to be used in the analysis, and there is a concern that the accuracy of the forming analysis results may be degraded to that in press forming.

Furthermore, in a case where the stress-strain curve data until reaching the strain region in which the uniform elongation is exceeded is obtained by approximating the data by the Swift equation from the stress-strain curve data of the strain region having uniform elongation obtained by the uniaxial tension test, it is difficult to obtain highly accurate stress-strain curve data across all of the strain regions. Therefore, it is necessary to select a strain region in which the relationship between the stress and the strain can be approximated in accordance with an object of the finite element method.

However, even when the strain region is selected in accordance with the object of the finite element method, the relationship between the stress and the strain is approximated, and the forming analysis, such as the press forming, the sheet forging, and the cold forging, is performed based on the approximate curve data, and in a case where the approximation accuracy other than the approximation accuracy in the selected strain region is remarkably low, there is a concern that generation of forming defects may not be able to be correctly detected in the press forming, the sheet forging, and the cold forging.

In addition, as a work hardening law other than the Swift equation, a Voce equation described in Non-Patent Document 4 is known. However, an object of the Voce equation is to improve the approximation accuracy of the stress-strain curve data of the strain region from the yield point of aluminum or an aluminum alloy until reaching the uniform elongation, and similar to the Swift equation, there is a problem in the approximation accuracy including a strain region in which uniform elongation has been exceeded.

Furthermore, as work hardening law other than the Swift equation, a complex hardening law of Lemaitre-Chaboche is also known. However, the complex hardening law of Lemaitre-Chaboche has an excellent approximation accuracy regarding a Bauschinger effect which is a phenomenon of deterioration of yield stress when an inverse load is applied, but the approximation accuracy of the stress-strain curve data including the strain region in which the uniform elongation is exceeded is not excellent.

PRIOR ART DOCUMENT

Patent Document

[Patent Document 1] Japanese Examined Patent Application, Second Publication No. 8-16644

Non-Patent Document

[Non-Patent Document 1] Yoshida and Itou, "Material models in sheet forming simulation", Plasticity and Process, Vol. 40, No. 460, pp. 34-39

[Non-Patent Document 2] Yoshida, Yoshii, Komorida, and Usuda, "Deformation form dependence (hardening anisotropy X) of hardening strength, and application thereof to formability evaluation", Plasticity and Process, Vol. 11, No. 114, pp. 513-521

[Non-Patent Document 3] Yoshida, Yoshii, Usuda, and Watanabe, "Second axial tension n and c, and application thereof to formability evaluation" Plasticity and Process, Vol. 11, No. 116. pp. 670-675

[Non-Patent Document 4] B. K. Choudhary, et. al, "Tensile stress-strain and work hardening behaviour of 316LN austenitic stainless steel", materials Science and Technology, February 2001, Vol.17, pp. 223-231

DISCLOSURE OF THE INVENTION

Problems to be Solved by the Invention

Considering the above-described situation, an object of the present invention is to provide an evaluation method of a plastic material which can obtain highly accurate stress-strain curve data until reaching a strain region in which uniform elongation is exceeded, and an evaluation method of deformation processing of a plastic material which can perform forming analysis of deformation processing with high accuracy based on the stress-strain curve data obtained by the evaluation method of the plastic material.

Means for Solving the Problem

An outline of the present invention is as follows.

(1) A first embodiment of the present invention is an evaluation method of a plastic material including: a first shearing process of performing simple shearing deformation with respect to a first plastic sheet by dividing the first plastic sheet having a first strain amount which includes 0 into two regions by a virtual section perpendicular to a surface thereof, and by applying a shear stress to the first plastic sheet so as to make relative positions of the two regions shifted along the virtual section be on the same surface; a second shearing process of performing simple shearing deformation with respect to a second plastic sheet by dividing the second plastic sheet having a second strain amount which is different from the first strain amount and includes 0 into two regions by a virtual section perpendicular to a surface thereof, and by applying a shear stress to the second plastic sheet so as to make relative positions of the two regions shifted along the virtual section be on the same surface; a first partial stress-strain curve data obtaining process of obtaining first partial stress-strain curve data from a relationship between the shear stress applied to the first plastic sheet in the first shearing process, and a total strain amount which is a sum of a shear strain amount which is applied to the first plastic sheet in the first shearing process and the first strain amount, by measuring the shear stress and the shear strain which are applied to the first plastic sheet in the first shearing process; a second partial stress-strain curve data obtaining process of obtaining second partial stress-strain curve data from a relationship between the shear stress applied to the second plastic sheet in the second shearing process, and a total strain amount which is a sum of a shear strain amount which is applied to the second plastic sheet in the second shearing process and the second strain amount, by measuring the shear stress and the shear strain which are applied to the second plastic sheet in the second shearing process; and a synthesized stress-strain curve data obtaining process of obtaining synthesized stress-strain curve data based on the first partial stress-strain curve data and the second partial stress-strain curve data.

(2) The evaluation method of a plastic material according to the above-described (1) may further include: an outer form removing process of obtaining the second plastic sheet by removing an outer form part of the first plastic sheet after unloading the shear stress applied in the first shearing process.

(3) In the evaluation method of a plastic material according to the above-described (2), in the outer form removing process, the outer form part may be removed across the two regions of the first plastic sheet along the surface direction perpendicularly intersecting the virtual section and a flat surface of the first plastic sheet.

(4) In the evaluation method of a plastic material according to the above-described (1), the first plastic sheet and the second plastic sheet may be individual plastic sheets different from each other.

(5) In the evaluation method of a plastic material according to the above-described (4), the second strain amount is greater than the first strain amount, and is equal to or less than the strain amount applied to the first plastic sheet in the first shearing process.

(6) In the evaluation method of a plastic material according to the above-described (4), in the synthesized stress-strain curve data obtaining process, the synthesized stress-strain curve data may be obtained by combining the curve data of a strain region other than a part which receives the influence of a cross-over effect from the first partial stress-strain curve data and the second partial stress-strain curve data.

(7) The evaluation method of a plastic material according to the above-described (4) may further include: an outer form removing process of obtaining a third plastic sheet having a third strain amount different from the first strain amount and the second strain amount by removing an outer form part formed by the simple shearing deformation in the first plastic sheet; a third shearing process of performing simple shearing deformation with respect to the third plastic sheet by dividing the third plastic sheet into two regions by a virtual section perpendicular to the surface thereof, and by applying a shear stress to the third plastic sheet so as to make relative positions of the two regions shifted along the virtual section be on the same surface; and a third partial stress-strain curve data obtaining process of obtaining third partial stress-strain curve data from a relationship between the shear stress applied to the third plastic sheet in the third shearing process, and a total strain amount which is a sum of a shear strain amount which is applied to the third plastic sheet in the third shearing process and the third strain amount, by measuring the shear stress and the shear strain which are applied to the third plastic sheet in the third shearing process, and in the synthesized stress-strain curve data obtaining process, the synthesized stress-strain curve data may be obtained based on the first partial stress-strain curve data, the second partial stress-strain curve data, and the third partial stress-strain curve data.

(8) In the evaluation method of a plastic material according to the above-described (1), in the synthesized stress-strain curve data obtaining process, the synthesized stress-strain curve data is obtained by approximating the first partial stress-strain curve data and the second partial stress-strain curve data based on a work hardening law.

(9) In the evaluation method of a plastic material according to the above-described (1), in the synthesized stress-strain curve data obtaining process, the synthesized stress-strain curve data is obtained by approximating the first partial stress-strain curve data and the second partial stress-strain curve data by a relational equation expressed by the following equation (A).

$$\sigma = K(\varepsilon^P + a)^m \quad (A)$$

$$m = n^* + 1/\{b(\varepsilon^P + c)\} \quad (B)$$

here, in equation (A), σ is an equivalent stress, K (MPa) and a are material factors of the plastic material, $\varepsilon^P$ is an equivalent plastic strain, and m is as illustrated in the above-described equation (B), and in equation (B), n* is a convergence value of a work hardening coefficient, b is a parameter indicating the rate of convergence of the work hardening coefficient, and c is a parameter indicating the rate of development of the work hardening coefficient.

(10) In the evaluation method of a plastic material according to the above-described (1), the application direction of the shear stress in the first shearing process and the application direction of the shear stress in the second shearing process may be opposite to each other.

(11) In the evaluation method of a plastic material according to the above-described (1), in the first shearing process, the application direction of the shear stress may be reversed in the middle.

(12) In the evaluation method of a plastic material according to the above-described (10) or (11), in the synthesized stress-strain curve data obtaining process, the synthesized stress-strain curve data may be obtained by approximating the first partial stress-strain curve data and the second partial stress-strain curve data based on a kinematic hardening law.

(13) In the evaluation method of a plastic material according to the above-described (1), the first plastic sheet and the second plastic sheet may have a shape of a rectangular flat surface.

(14) In the evaluation method of a plastic material according to the above-described (1), in the first shearing process and the second shearing process, the largest amount of change in the sheet thickness of the first plastic sheet and the second plastic sheet may be equal to or less than 1% of the sheet thickness.

(15) In the evaluation method of a plastic material according to the above-described (1), the shear strain applied in each of the first shearing process and the second shearing process, may be in a range of 0.4 to 1.2.

(16) In the evaluation method of a plastic material according to the above-described (1), the first plastic sheet and the second plastic sheet may be steel sheets.

(17) A second embodiment of the present invention is an evaluation method of deformation processing of a plastic material, in which a computer provided with an analyzer which performs forming analysis of deformation processing of the plastic material by a finite element method is used, in which the synthesized stress-strain curve data obtained by the evaluation method of the plastic material according to any one of the above-described (1) to (16) is input to the analyzer of the computer, and in which the analyzer is operated by the computer.

(18) In the evaluation method of deformation processing of a plastic material according to the above-described (17), the forming analysis may obtain at least one of a strain distribution, the maximum strain, and a forming load of the plastic material in a case where the deformation processing is performed with respect to the plastic material.

(19) A third embodiment of the present invention is an evaluation method of a plastic material comprising: a first shearing process of performing simple shearing deformation with respect to a first plastic sheet by dividing the first plastic sheet having a first strain amount which includes 0 into two regions by a virtual section perpendicular to a surface thereof, and by applying shear stress to the first plastic sheet so as to make relative positions of the two regions shifted along the virtual section be on the same surface; a first partial stress-strain curve data obtaining process of obtaining first partial stress-strain curve data from a relationship between the shear stress applied to the first plastic sheet in the first shearing process, and a total strain amount which is a sum of a shear strain amount which is applied to the first plastic sheet in the first shearing process and the first strain amount, by measuring the shear stress and the shear strain which are applied to the first plastic sheet in the first shearing process; and a synthesized stress-strain curve data obtaining process of obtaining synthesized stress-strain curve data by approximating the first partial stress-strain curve data by a relational equation expressed by the following equation (C).

$$\sigma = K(\varepsilon^P + a)^m \quad (C)$$

$$m = n^* + 1/\{b(\varepsilon^P + c)\} \quad (D)$$

here, in equation (C), σ is an equivalent stress, K (MPa) and a are material factors of the plastic material, $\varepsilon^P$ is an equivalent plastic strain, and m is as illustrated in the above-described equation (D), and in equation (D), n* is a convergence value of a work hardening coefficient, b is a parameter indicating the rate of convergence of the work hardening coefficient, and c is a parameter indicating the rate of development of the work hardening coefficient.

(20) A fourth embodiment of the present invention is an evaluation method of deformation processing of a plastic material, in which a computer provided with an analyzer which performs forming analysis of deformation processing of the plastic material by a finite element method is used, in which the synthesized stress-strain curve data obtained by the evaluation method of the plastic material according to the above-described (19) is input to the analyzer of the computer, and in which the analyzer is operated by the computer.

(21) In the evaluation method of deformation processing of a plastic material according to the above-described (20), the forming analysis may obtain at least one of a strain distribution, the maximum strain, and a forming load of the plastic material in a case where deformation processing is performed with respect to the plastic material.

Effects of the Invention

According to the evaluation method of a plastic material described in the above (1), by performing the shearing process at least two times with respect to the first plastic sheet and the second plastic sheet having strain amounts different from each other, it is possible to obtain at least two pieces of partial stress-strain curve data having different strain regions from each other. By obtaining the synthesized stress-strain curve data based on the partial stress-strain curve data, for example, it is possible to obtain the relationship between the shear stress and the shear strain until reaching the strain region in which the uniform elongation is exceeded in a tension test in the related art.

According to the evaluation method of a plastic material described in the above (2), by performing the outer form removing process which is performed with respect to the first plastic sheet after the first shearing process, it is possible to obtain the second plastic sheet in which cracks which are starting points of fracture are removed. Therefore, since it is possible to repeatedly perform the shearing process with respect to one plastic sheet, it is possible to reduce the number of plastic sheets prepared in advance. In addition, since the strain regions of the first partial stress-strain curve data and the second partial stress-strain curve data do not overlap each other and are not separated from each other, it is possible to obtain synthesized stress-strain curve data over a wide range of the strain region by a small number of tests with high accuracy.

According to the evaluation method of a plastic material described in the above (3), since crack are removed across two regions of the first plastic sheet along the surface direction perpendicularly intersecting the virtual section and the flat surface of the first plastic sheet, it is possible to more reliably remove cracks which are starting points of fractures.

According to the evaluation method of a plastic material described in the above (4), it is possible to obtain plural pieces of partial stress-strain curve data by the actual measurement by performing the simple shearing deformation with respect to each of the plurality of plastic sheets having strain amounts different from each other. Therefore, it is possible to obtain synthesized stress-strain curve data over a wide range of the strain region based on the partial stress-strain curve data.

According to the evaluation method of a plastic material described in the above (5), since the strain region of the first partial stress-strain curve data and the strain region of the second partial stress-strain curve data overlap each other, it is possible to avoid the separation of the strain regions of the first partial stress-strain curve data and the second partial stress-strain curve data from each other. Therefore, it is possible to obtain the synthesized stress-strain curve data over a wide range of the strain region.

According to the evaluation method of a plastic material described in the above (6), in the synthesized stress-strain curve data obtaining process, since the curve data of the strain region other than the part which receives the influence of a cross-over effect is combined from each piece of partial stress-strain curve data, it is possible to obtain synthesized stress-strain curve data with a small amount of error.

According to the evaluation method of a plastic material described in the above (7), by performing the outer form removing process with respect to the first plastic sheet after the first shearing process, it is possible to obtain the third plastic sheet of which cracks which are the starting points of the fracture are removed. Therefore, since it is possible to repeatedly perform the shearing process with respect to one plastic sheet, it is possible to reduce the number of plastic sheets to be prepared in advance. In addition, since the strain regions of the first partial stress-strain curve data and the third partial stress-strain curve data do not overlap each other and are not separated from each other, it is possible to obtain synthesized stress-strain curve data over a wide range of the strain region by a small number of tests with high accuracy.

According to the evaluation method of a plastic material described in the above (8), since the first partial stress-strain curve data and the second partial stress-strain curve data are approximated based on a work hardening law, it is possible to obtain a wider range of the synthesized stress-strain curve data.

According to the evaluation method of a plastic material described in the above (9), since the first partial stress-strain curve data and the second partial stress-strain curve data are approximated based on the above-described equation (A) it is possible to obtain a wider range of the synthesized stress-strain curve data with high accuracy.

According to the evaluation method of a plastic material described in the above (10), it is possible to obtain the synthesized stress-strain curve data when an inverse load is applied. Therefore, it is possible to evaluate a Bauschinger effect which is a phenomenon of deterioration of yield stress when the inverse load is applied.

According to the evaluation method of a plastic material described in the above (11), it is possible to obtain the synthesized stress-strain curve data when the inverse load is applied. Therefore, it is possible to evaluate a Bauschinger effect which is a phenomenon of deterioration of the yield stress when the inverse load is applied. In particular, since it is possible to reverse the load direction at the time when a desirable amount of strain amount is loaded, it is possible to obtain synthesized stress-strain curve data having higher practicability.

According to the evaluation method of a plastic material described in the above (12), since the partial stress-strain curve data obtained in the above-described (10) or (11) is approximated based on the kinematic hardening law, it is possible to obtain a wider range of synthesized stress-strain curve data.

According to the evaluation method of a plastic material described in the above (13), since each of the plastic sheets have a shape of a rectangular flat surface, it is possible to suppress generation of cracks which can be the starting points of the fracture when the shearing processing is performed.

According to the evaluation method of a plastic material described in the above (14), since an amount of decrease of the sheet thickness of the plastic sheet is reduced in each shearing process, necking is not generated in the sheet thickness direction. Therefore, it is also possible to obtain the partial stress-strain curve data in a wide strain region by a uniaxial tension test. Therefore, the number of shearing processes does not increase, the metal sheet does not fracture in the shearing process, and it is possible to obtain a wide range for the synthesized stress-strain curve data.

According to the evaluation method of a plastic material described in the above (15), since the shear strain per one instance in each shearing process is in a range of 0.4 to 1.2, the number of shearing processes does not increase, the metal sheet does not fracture in the shearing process, and it is possible to obtain a wide range for the synthesized stress-strain curve data.

According to the evaluation method of a plastic material described in the above (16), since the steel sheet is used as the plastic sheet, it is possible to obtain synthesized stress-strain curve data of the steel.

According to the evaluation method of deformation processing of a plastic material described in the above (17), by inputting the synthesized stress-strain curve data obtained by the evaluation method of the plastic materials described in any one of the above-described (1) to (16) to the computer, it is possible to perform the forming analysis in a case where the deformation processing is performed with respect to the plastic material with a high strain amount, with high accuracy.

According to the evaluation method of deformation processing of a plastic material described in the above (18), it is possible to correctly predict at least one of the strain distribution, the maximum strain, and the forming load of the plastic material when the deformation processing is performed with respect to the plastic material. For example, in a case where the press forming is employed as the deformation processing, it is possible to correctly predict the strain distribution and the maximum strain of the plastic sheet in the press forming, and to correctly detect generation of cracks. In addition, in a case where sheet forging or cold forging is employed as the deformation processing, for example, by obtaining the forming load with respect to the plastic material due to a form, it is possible to correctly predict the forming load required for the processing.

According to the evaluation method of a plastic material described in the above (19), since the first partial stress-strain curve data is approximated based on the above-described equation (C), it is possible to obtain a wide range for the synthesized stress-strain curve data with high accuracy.

According to the evaluation method of deformation processing of a plastic material described in the above (20), by inputting the synthesized stress-strain curve data obtained by the evaluation method of the plastic material according to above-described (19) to the computer, it is possible to perform the forming analysis in a case where the deformation processing is performed with respect to the plastic material with a high strain amount, with high accuracy.

Furthermore, according to the evaluation method of deformation processing of a plastic material described in the above (21), it is possible to correctly predict at least one of the strain distribution, the maximum strain, and the forming load when the deformation processing is performed with respect to the plastic material. For example, in a case where the press forming is employed as the deformation processing, it is possible to predict the strain distribution and the maximum strain of the plastic sheet in the press forming, and to correctly detect generation of cracks. In addition, in a case where sheet forging or cold forging is employed as the deformation processing, for example, by obtaining the forming load with respect to the plastic material due to a form, it is possible to correctly predict the forming load required for the processing.

EMBODIMENTS OF THE INVENTION

In forming analysis of plastic material processing which uses finite element analysis, stress-strain curve data to a strain region having uniform elongation of a uniaxial tension test is used from the stress-strain curve data. However, for example, in press forming of an actual plastic material, sheet forging and cold forging, a strain much greater than that of the strain region having uniform elongation is applied to a plastic material. Therefore, in the related art, in a case where the forming analysis, such as the press forming which uses the finite element method, the sheet forging, and the cold forging, is performed, by extrapolating the stress-strain curve data of the strain region having uniform elongation to a strain region in which the uniform elongation is exceeded, the stress-strain curve data is approximated considering the influence of the work hardening, and the finite element analysis is performed by using the approximate curve data.

As a method for extrapolating the stress-strain curve data until reaching the strain region in which the uniform elongation is exceeded, for example, a method for obtaining average inclination of a stress-strain curve of the strain region having uniform elongation, and extrapolating a straight line having the average inclination until reaching the strain region in which the uniform elongation is exceeded, may be employed. In addition, as another method, a method for obtaining a partial inclination of the stress-strain curve of the strain region having uniform elongation, and extrapolating the straight line having the inclination until reaching the strain region in which the uniform elongation is exceeded, may be employed. An example of the approximate curve data is illustrated in FIG. 1.

Figure 1:
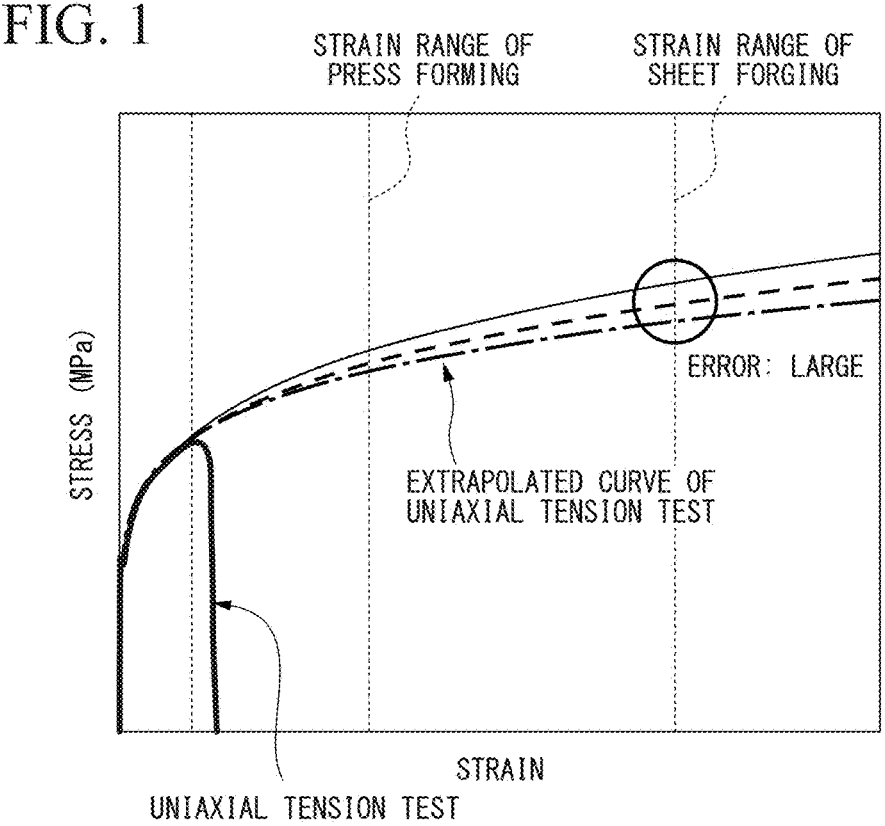
FIG. 1 is a graph illustrating an example of stress-strain curve data obtained by a uniaxial tension test, and extrapolated curve data obtained by extrapolating the stress-strain curve data.

In FIG. 1, the stress-strain curve data obtained by the uniaxial tension test and extrapolated curve data extrapolated from the stress-strain curve data of the uniaxial tension test, are illustrated. As illustrated in FIG. 1, in the extrapolated curve data, unevenness is generated according to a calculation method thereof, and the unevenness increases as the strain amount increase. In particular, in the strain region of the sheet forging, there is a case where flow stress varies by a width which is equal to or greater than 10%.

The stress-strain curve data decreases after exceeding the maximum tensile strength. The reason thereof is that plastic instability occurs and local necking occurs in a test piece when a strain greater than a strain which corresponds to the maximum tensile strength is applied. Instead of the uniaxial tension test, a method for obtaining the stress-strain curve data by a hydraulic bulging test is also employed, but this method merely obtains the stress-strain curve data of the strain region which is approximately two times the strain region having uniform elongation. Furthermore, a method for obtaining the stress-strain curve data by the cylindrical upsetting test is also employed, but for example, in order to obtain the stress-strain curve data of a steel sheet by the method, it is necessary to prepare a cylindrical body of which the diameter is approximately the thickness of the steel sheet as the test piece, and much labor and costs are required for adjusting the test piece.

In addition, for example, in a case where the deformation processing is performed with respect to the steel sheet, there is a case where cracks are generated in the steel sheet. In particular, cracks are likely to be generated in the press forming with respect to a high-strength steel sheet. There is a case where a strain amount applied to the location at which cracks are generated when the press forming is performed, reaches approximately four times that of the strain region of the stress-strain curve data obtained by the uniaxial tension test. Therefore, in a case where the forming analysis in a case where the press forming is performed with respect to the steel sheet is performed by the finite element method or the like, the extrapolated stress-strain curve data is used, but since the stress-strain curve data is merely extrapolated stress-strain curve data and is not actually measured data, there is a concern that an error occurs.

Here, the inventors investigated a method for obtaining the stress-strain curve data in a wide strain region, and found that it is more advantageous to use the simple shearing test than the uniaxial tension test of the related art. This is because a simple shearing test applies an in-plane shear stress to a plastic sheet, and even when applying the strain greater than the strain which corresponds to the maximum tensile strength, necking does not occur in the sheet thickness direction.

Furthermore, the inventors found that highly accurate synthesized stress-strain curve data is obtained across the wide strain region without performing the approximation, such as the extrapolation, by obtaining plural pieces of partial stress-strain curve data (a) by performing the simple shearing test with respect to the plastic sheets by preparing the same type of plural plastic sheets having strain amounts different from each other, or (b) by repeating simple shearing deformation again with respect to a single plastic sheet by removing an outer form part deformed after the simple shearing test, and by obtaining one piece of synthesized stress-strain curve data based on the partial stress-strain curve data.

Furthermore, the inventors have found an approximation having higher accuracy than that of the approximation of the related art, such as the Swift equation, as a result of analyzing highly accurate synthesized stress-strain curve data which is actually obtained by the above-described method.

The present invention is based on the above-described discovery.

Hereinafter, the present invention will be described in detail based on a first embodiment to a sixth embodiment.

Furthermore, in any embodiment, steel (that is, the steel sheet which is the plastic sheet) which is the plastic material is used, but as the plastic material, it is possible to use a metal material, such as aluminum or titanium, a glass fiber-reinforcing resin material, such as FRP or FRTP, and further, a composite material thereof.

In addition, in the specification, the "partial stress-strain curve data" means data which is obtained by performing the shearing process one time, and which indicates a relationship between the stress and the strain. In addition, the "synthesized stress-strain curve data" means stress-strain curve data which is combined by the plural pieces of partial stress-strain curve data, or which has a wide strain region obtained by employing the approximation to at least one piece of partial stress-strain curve data.

(First Embodiment)

Hereinafter, an evaluation method of the steel according to the first embodiment of the present invention will be described with reference to FIGS. 2 to 7.

The evaluation method of the steel according to the embodiment includes: [1-1] a first shearing process of performing the shearing deformation with respect to a first steel sheet 101; [1-2] a partial stress-strain curve data obtaining process of obtaining first partial stress-strain curve data from a measurement result of the first shearing process; [1-3] an outer form removing process of removing the outer form part of first steel sheet 101 after the shearing deformation, and obtaining a second steel sheet 102; [1-4] a second shearing process of performing the shearing deformation with respect to the second steel sheet 102; [1-5] a partial stress-strain curve data obtaining process of obtaining second partial stress-strain curve data from a measurement result of the second shearing process; and [1-6] a synthesized stress-strain curve data obtaining process of obtaining synthesized stress-strain curve data based on the first partial stress-strain curve data and the second partial stress-strain curve data. Hereinafter, each process will be described in detail.

[1-1] First Shearing Process

Figure 2:
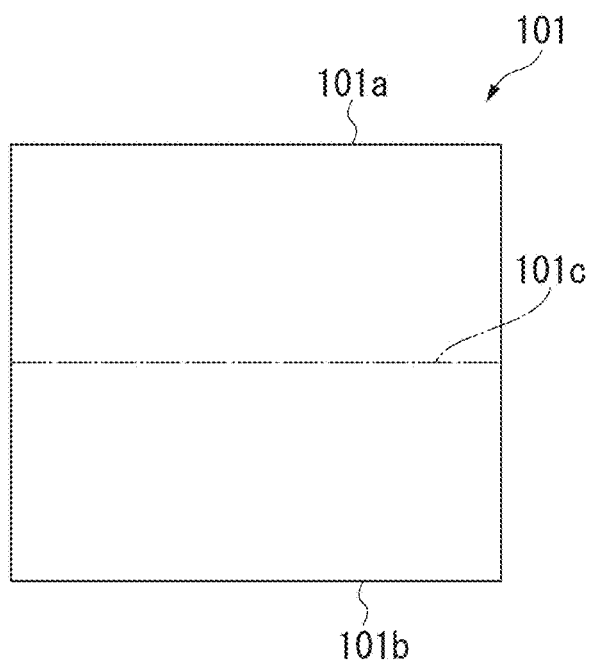
FIG. 2 is a plan view illustrating a first steel sheet which is used in an evaluation method of steel according to a first embodiment of the present invention.

As illustrated in FIG. 2, the first steel sheet 101 is a steel sheet having a shape of a rectangular flat surface. The preliminary strain may be applied to the first steel sheet 101 as necessary. In other words, the first steel sheet 101 has a first strain amount (which may include 0).

As illustrated in FIG. 2, between one side 101a and the other side 101b of the first steel sheet 101, a virtual section 101c which divides the first steel sheet 101 into two regions is set. The virtual section 101c is set perpendicularly to the surface of the first steel sheet 101. In addition, in a case where the virtual section 101c is a boundary, a part including the one side 101a of the first steel sheet 101 and a part including the other side 101b are respectively bound by a fixer which is schematically illustrated. As the fixer, a chucking device which grabs and fixes the first steel sheet 101 can be illustrated as an example.

Figure 3:
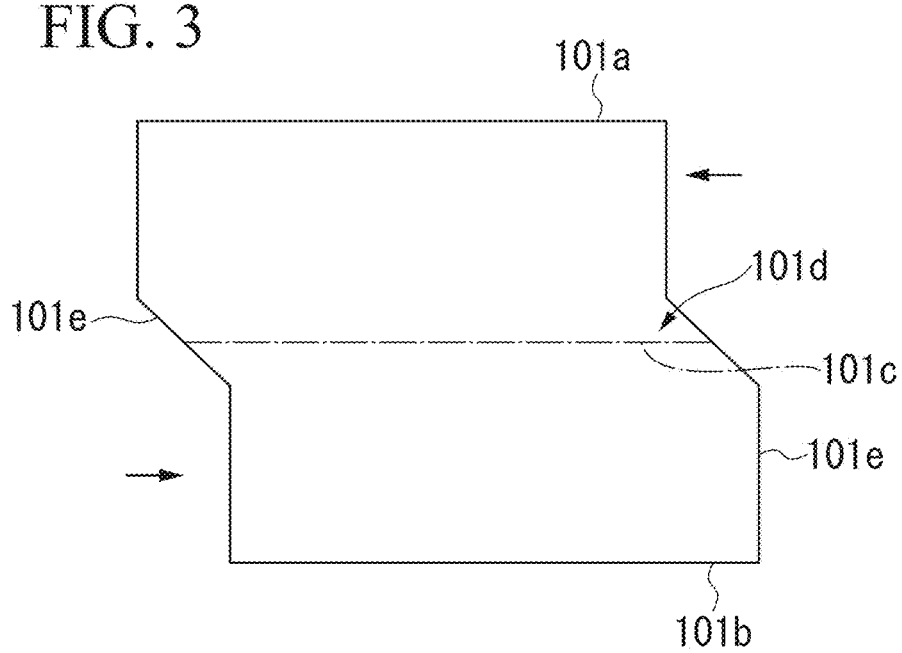
FIG. 3 is a plan view illustrating the first steel sheet to which a shear stress is applied.

Next, as illustrated in FIG. 3, the simple shearing deformation is performed with respect to the first steel sheet 101 by applying the shear stress to make the two regions of the first steel sheet 101 divided by the virtual section 101c shifted from each other in the sheet width direction along the virtual section 101c (that is, to make relative positions of the two regions shifted be on the same surface).

Specifically, in a state where each of the two regions of the first steel sheet 101 divided by the virtual section 101c is bound by the chucking device, the chucking devices are moved to be shifted from each other in the sheet width direction along the virtual section 101c. Accordingly, shearing deformation part 101d is formed near the virtual section 101c. Since the shear stress is applied in the sheet width direction along the 101c, the sheet thickness at the shearing deformation part 101d does not change compared to that before the stress is applied. Furthermore, there is also a case where the sheet thickness can decrease according to the material, but the largest amount of change in the sheet thickness is at most equal to or less than 1%. Therefore, the local necking does not occur in the test piece similar to a short axial tension test.

However, the shape of sides 101e and 101e which connect the one side 101a and the other side 101b of the first steel sheet 101 to each other, are largely deformed by applying the shear stress to the first steel sheet 101.

The shear strain applied to the first steel sheet 101 by performing shearing process one time is preferably in a range of 0.4 to 1.2, and is more preferably in a range of 0.5 to 1.0. When the applying amount of the shear strain performed one time is set to be equal to or greater than 0.4, the strain amount due to the shearing deformation performed one time does not become extremely small, and the number of repeats of the shearing process and the outer form removing process does not increase. In addition, when the applying amount of the shear strain per one instance is set to be equal to or less than 1.2, it is possible to prevent the fracture of the steel sheet in an early stage.

[1-2] First Partial Stress-strain Curve Data Obtaining Process

In the first partial stress-strain curve data obtaining process, the shear stress and the shear strain which are applied to the first steel sheet 101 in the above-described first shearing process, are measured. In addition, the first partial stress-strain curve data is obtained from a relationship between (1) the shear stress applied to the first steel sheet 101 in the first shearing process, and (2) the total strain amount which is a sum of the shear strain amount which is applied to the first steel sheet 101 in the first shearing process and the first strain amount.

[1-3] Outer Form Removing Process

Figure 4:
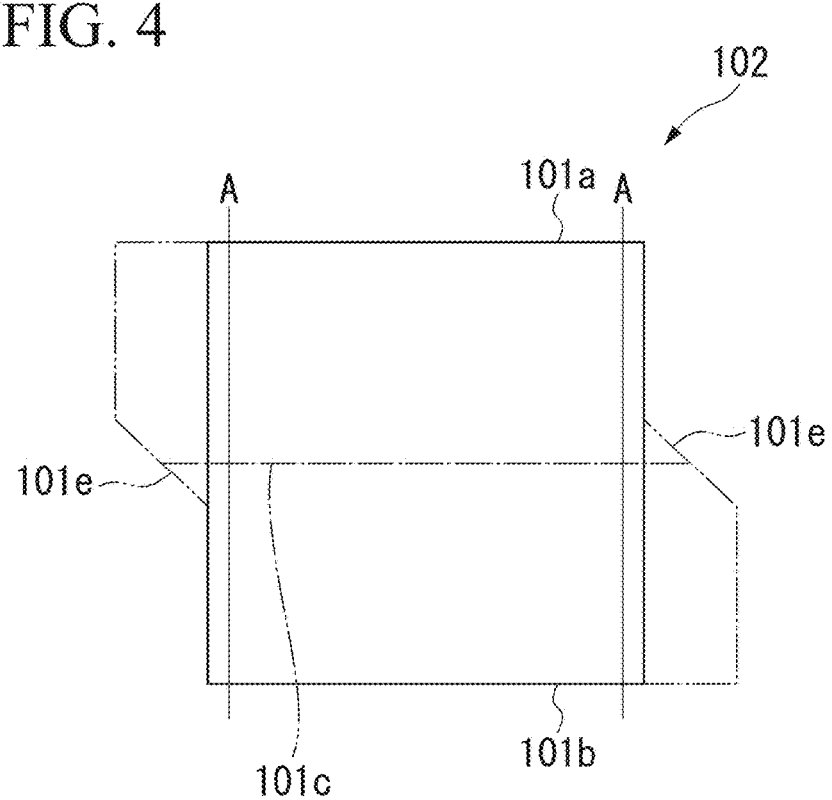
FIG. 4 is a plan view illustrating a second steel sheet obtained by removing an outer form part of the first steel sheet.

In the outer form removing process, as illustrated in FIG. 4, by removing the outer form part deformed by applying the shear stress after unloading the shear stress first, the second steel sheet 102 having a shape of a rectangular flat plane is obtained. Specifically, by cutting off the part including the sides 101e and 101e in the first steel sheet after the first shearing process, the shape of the first steel sheet 101 in a plan view becomes a rectangular shape.

Among the sides 101e and 101e which are deformed by applying the shear stress in the first shearing process, there is a possibility that cracks are generated at a location at which the deformation is particularly large. In a state where cracks remain, in the second shearing process which will be described later, there is a concern that the second steel sheet 102 fractures considering cracks as starting points. However, by performing the outer form removing process, since it is possible to obtain the second steel sheet 102 of which cracks which are the starting points of the fracture are removed, it is possible to solve the above-described problem.

Furthermore, in the outer form removing process, the outer form part may be removed across the two regions of the first steel sheet 101 along the surface direction perpendicularly intersecting the virtual section 101c and the flat surface of the first steel sheet 101. In other words, the outer form part may be removed along two lines A in FIG. 4. Accordingly, it is possible to more reliably remove cracks which are the starting points of the fracture.

[1-4] Second Shearing Process

In the second shearing process, the shear stress is applied to the second steel sheet 102 obtained by the outer form removing process by a method similar to the method described in the above [1-1].

The second steel sheet 102 has the second strain amount which is caused by the strain applied in the first shearing process. Therefore, in the embodiment, the second strain amount of the second steel sheet 102 is greater than the first strain amount of the above-described first steel sheet 101.

[1-5] Second Partial Stress-Strain Curve Data Obtaining Process

In the second partial stress-strain curve data obtaining process, the shear stress and the shear strain which are applied to the second steel sheet 102 in the second shearing process, are measured. In addition, the second partial stress-strain curve data is obtained from a relationship between (1) the shear stress applied to the second steel sheet 102 in the second shearing process, and (2) the total strain amount which is a sum of the shear strain amount which is applied to the second steel sheet 102 in the second shearing process and the second strain amount.

[1-6] Synthesized Stress-Strain Curve Data Obtaining Process

In the synthesized stress-strain curve data obtaining process, the synthesized stress-strain curve data is obtained at least based on the first partial stress-strain curve data and the second partial stress-strain curve data.

In the description above, the synthesized stress-strain curve data is obtained based on the two pieces of partial stress-strain curve data obtained by performing the shearing process two times during the outer form removing process, but according to the embodiment, it is possible to repeat the shearing process and the outer form removing process with respect to one steel sheet plural times. It is not necessary to particularly determine an upper limit of the number of repeats, the processing may continue until the steel sheet fractures during applying the shear stress.

Therefore, according to the evaluation method of the steel according to the embodiment, it is possible to reduce the number of plastic sheets to be prepared in advance. In addition, since the strain region of the first partial stress-strain curve data and the strain region of the second partial stress-strain curve data do not overlap each other and are not separated from each other, it is possible to obtain the synthesized stress-strain curve data over a wide range of the strain region by small number of tests with high accuracy.

Figure 5:
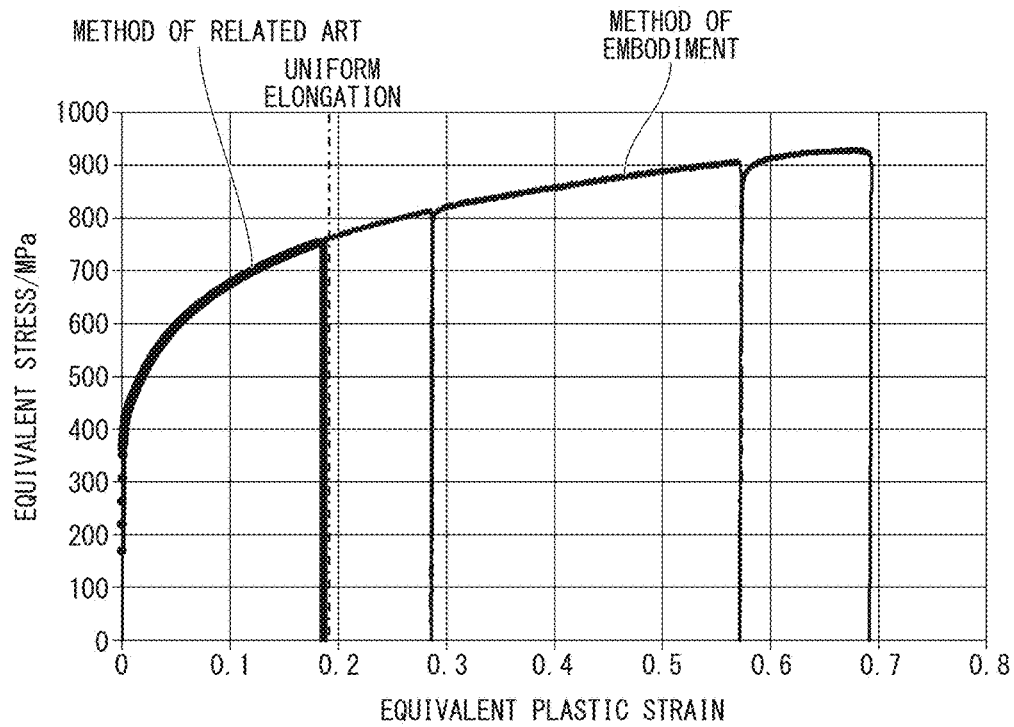
FIG. 5 is a graph illustrating synthesized stress-strain curve data obtained by the evaluation method of the steel according to the first embodiment of the present invention, and equivalent stress-equivalent plastic strain curve data obtained by a method of the related art.

In FIG. 5, regarding a case (method of the embodiment) where the shearing process is repeated three times during the two times of outer form removing process, and a case (method in the related art) where the simple tension test is performed, the obtained equivalent stress-equivalent plastic strain curve data is illustrated. In the steel sheet supplied for the test, the tensile strength is 600 MPa, the yield strength is 400 MPa, and the sheet thickness is 1.6 mm.

As illustrated in FIG. 5, in the method of the related art, the stress-strain curve data to an equivalent plastic strain of 0.19 is obtained, but according to the method of the embodiment, it is possible to obtain the stress-strain curve data to approximately 0.7 which is four times thereof.

Figure 6:
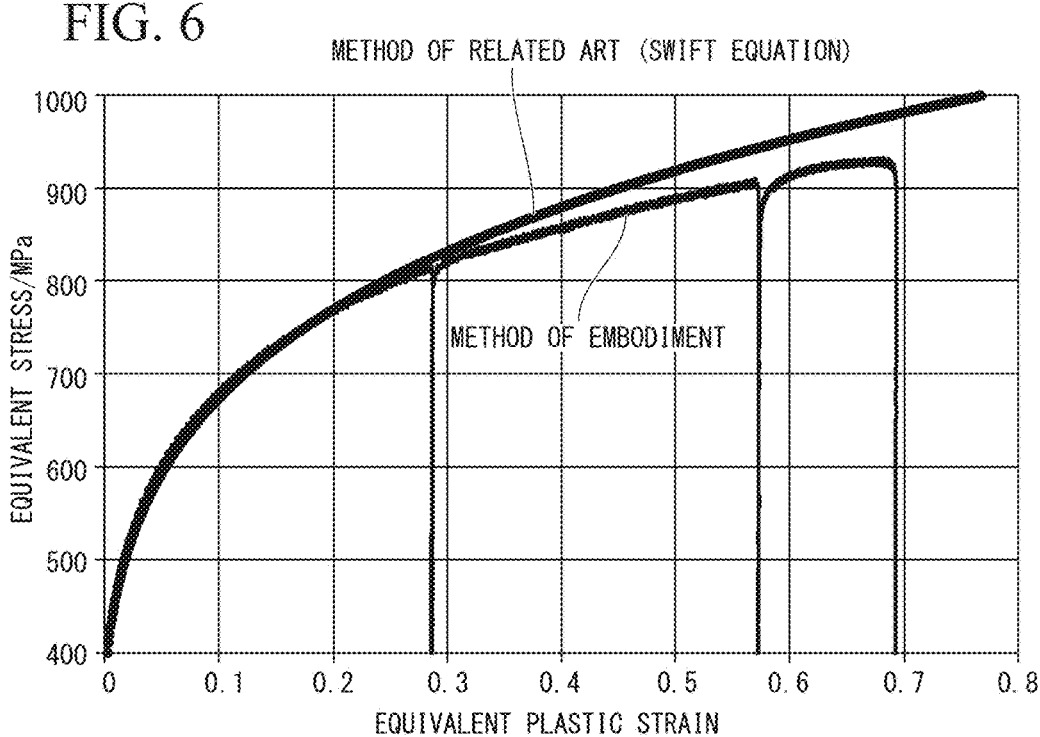
FIG. 6 is a graph illustrating the synthesized stress-strain curve data obtained by the evaluation method of the steel according to the first embodiment of the present invention, and equivalent stress-equivalent plastic strain curve data obtained by extrapolating the equivalent stress-equivalent plastic strain curve data obtained by the method of the related art based on a Swift equation.

Next, the equivalent stress-equivalent plastic strain curve data obtained according to the evaluation method of the steel according to the embodiment was investigated in detail. FIG. 6 illustrates the investigation result thereof. In FIG. 6, the synthesized stress-strain curve data obtained by the evaluation method of the steel according to the embodiment, and stress-strain curve data obtained by extrapolating and the stress-strain curve data to an equivalent plastic strain of 0.19 obtained by the method of the related art, until the plastic strain becomes equal to or greater than 0.7 based on a Swift equation, are illustrated.

The synthesized stress-strain curve data obtained by the evaluation method of the steel according to the embodiment is data which plots the equivalent stress and the equivalent plastic strain which are obtained from the shear stress and the shear strain which are actually measured. In addition, the extrapolated stress-strain curve data is data computed by applying the stress-strain curve data to the plastic strain of 0.1 obtained by the method of the related art, to the Swift equation of the following equation (1).

$$\sigma = \alpha(\varepsilon^P + \beta)^n \qquad (1)$$

here, in equation (1), $\sigma$ is an equivalent stress, $\alpha$ and $\beta$ are constants determined for each steel sheet, $\varepsilon^P$ is an equivalent plastic strain, and n is a work hardening coefficient.

As illustrated in FIG. 6, it is ascertained that the equivalent stress-equivalent plastic strain curve data extrapolated based on the Swift equation is separated from the synthesized stress-strain curve data obtained by the method of the embodiment when approaching a high-strain region.

Figure 7:
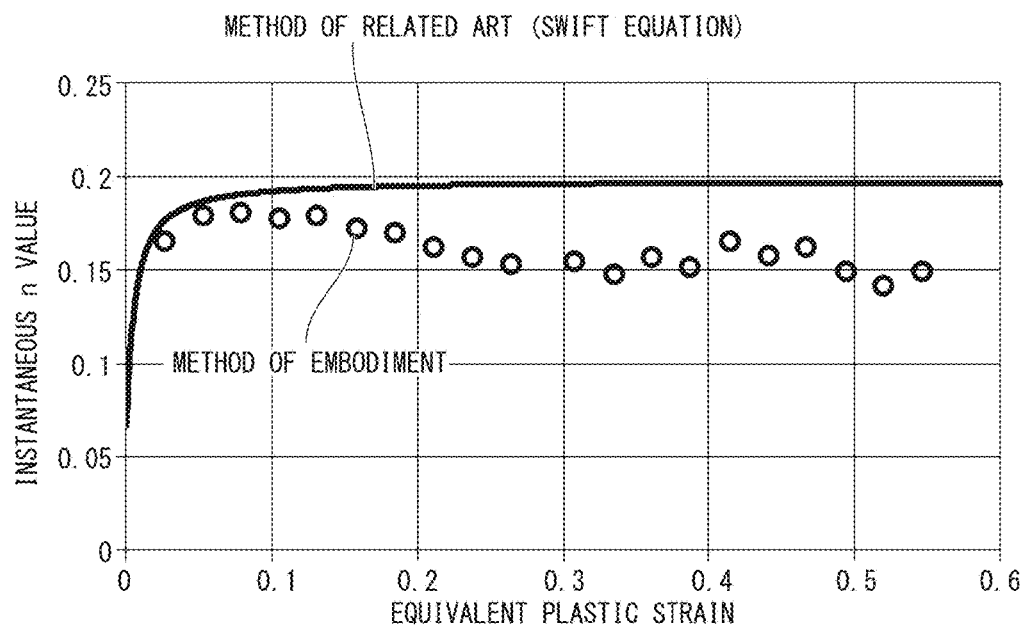
FIG. 7 is a graph illustrating a relationship between an instantaneous n value and an equivalent plastic strain.

The reason of the separation of the two pieces of curve data was investigated, and a relationship between an instantaneous n value and the equivalent plastic strain was investigated. The result thereof is illustrated in FIG. 7. The instantaneous n value is an instantaneous gradient in the curve data which plots the stress-strain curve data illustrated in FIG. 6 in both logarithmic graphs. As illustrated in FIG. 7, the stress-strain curve data extrapolate based on the Swift equation is converged to a substantially constant value as the strain amount increases. Meanwhile, the instantaneous n value of the stress-strain curve data obtained by the method of the embodiment tends to be converged as the strain amount increases, and continues to change without being converged to the constant value. The Swift equation is an equation on the assumption that the n value is constant, but it is ascertained that the Swift equation is not employed in a region in which the strain amount is particularly large in a case of the actual steel.

(Second Embodiment)

The evaluation method of the steel according to the second embodiment of the present invention is an evaluation method of the steel for obtaining the partial stress-strain curve data by preparing two or more steel sheets having the preliminary strain amounts different from each other, and by performing the simple shearing deformation with respect to each of the steel sheets, and further, for obtaining the synthesized stress-strain curve data based on the partial stress-strain curve data.

In addition, as a modification example, in the shearing process, similar to the first embodiment, the simple shearing deformation may be repeatedly performed again one or more times with respect to the steel sheet of which the outer form part of the steel sheet deformed by the simple shearing deformation is removed.

Figure 8:
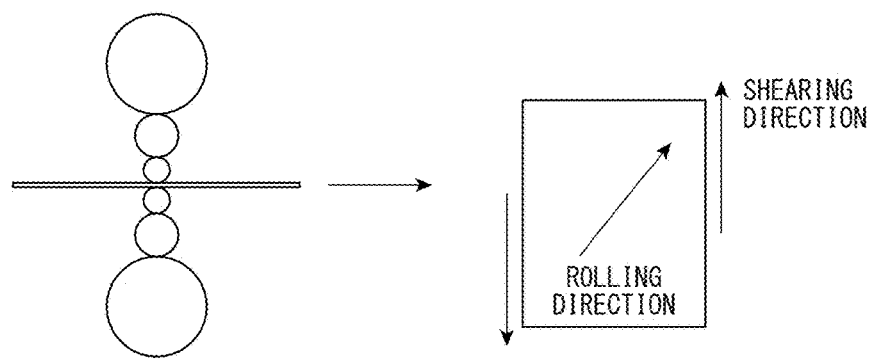
FIG. 8 is a schematic view illustrating a method for applying a preliminary strain to the steel sheet.

In the embodiment, unlike the first embodiment, two or more steel sheets of which the components and structures are the same, are prepared. One of the prepared steel sheets may be a steel sheet to which the strain amount is not applied. As a method for applying the preliminary strain to the steel sheet, as illustrated in FIG. 8, the rolling direction may be, for example, the direction which is not parallel to the shearing direction, and the rolling direction may be the direction parallel to the shearing direction.

In a case where n steel sheets are prepared, a plurality of steel sheets to which preliminary strains $\varepsilon^P_1$, $\varepsilon^P_2$, $\varepsilon^P_3$, ... $\varepsilon^P_n$ are gradually applied, are prepared. The number of steel sheets to be prepared may be determined in accordance with the size of a target equivalent strain. In particular, in a case where the stress-strain curve data to the high equivalent strain region is obtained, the plurality of steel sheets to which the strains are applied in advance may be prepared.

Furthermore, the preliminary strain $\varepsilon^P$ applied to the steel sheet by the cold rolling is applied in the following equation (2) in a case where the sheet thickness before the rolling is $h_0$ and the sheet thickness after the rolling is h.

$$\varepsilon^P = (2/\sqrt{3}) \ln(h/h_0) \qquad (2)$$

Not being limited to the cold rolling, a method for applying the preliminary strain to the steel sheet is not particularly limited as long as the method is a method which can control the preliminary strain amount, and processing of applying tensile stress which uses the uniaxial tension test and the flat surface strain tension test, can be illustrated as an example.

Hereinafter, the evaluation method of the steel according to the second embodiment of the present invention will be described with reference to FIGS. 9 to 22.

The evaluation of the steel according to the embodiment includes: [2-1] a first shearing process of performing the shearing deformation with respect to a first steel sheet 201; [2-2] a partial stress-strain curve data obtaining process of obtaining first partial stress-strain curve data from a measurement result of the first shearing process; [2-3] a second shearing process of performing the shearing deformation with respect to a second steel sheet 202 which is prepared separately from the first steel sheet 201; [2-4] a partial stress-strain curve data obtaining process of obtaining second partial stress-strain curve data from a measurement result of the second shearing process; and [2-5] a synthesized stress-strain curve data obtaining process of obtaining synthesized stress-strain curve data based on the first partial stress-strain curve data and the second partial stress-strain curve data. Hereinafter, each process will be described in detail.

[2-1] First Shearing Process

Figure 9:
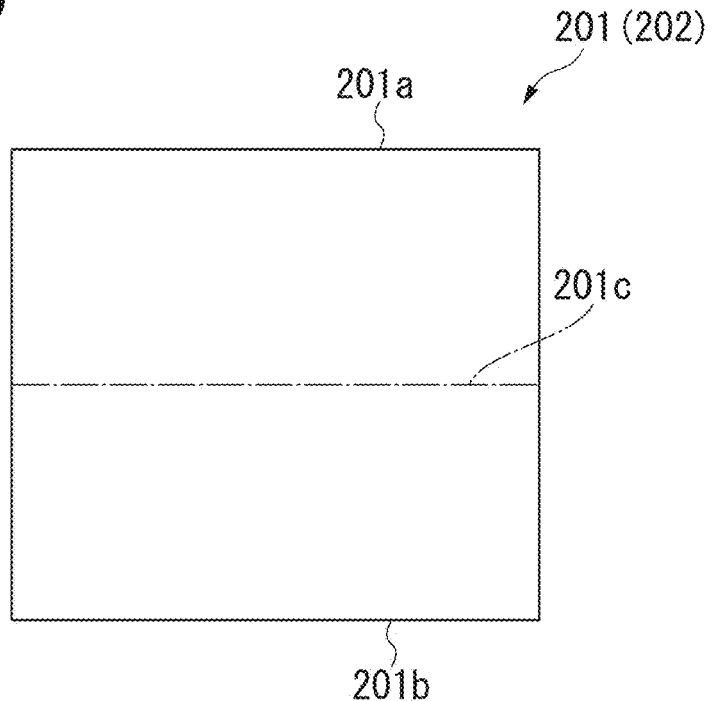
FIG. 9 is a plan view illustrating a first steel sheet (or second steel sheet) which is used in an evaluation method of the steel according to a second embodiment of the present invention.

As illustrated in FIG. 9, the first steel sheet 201 is a steel sheet having a shape of a rectangular flat surface. The preliminary strain may be applied to the first steel sheet 201 as necessary. In other words, the first steel sheet 201 has a first strain amount (which may include 0).

As illustrated in FIG. 9, between one side 201a and the other side 201b of the first steel sheet 201, a virtual section 201c which divides the first steel sheet 201 into two regions is set. The virtual section 201c is set perpendicularly to the surface of the first steel sheet 201. In addition, in a case where the virtual section 201c is a boundary, a part including the one side 201a of the first steel sheet 201 and a part including the other side 201b are respectively bound by a fixer which is schematically illustrated. As the fixer, a chucking device which grabs and fixes the first steel sheet 201 can be illustrated as an example.

Figure 10:
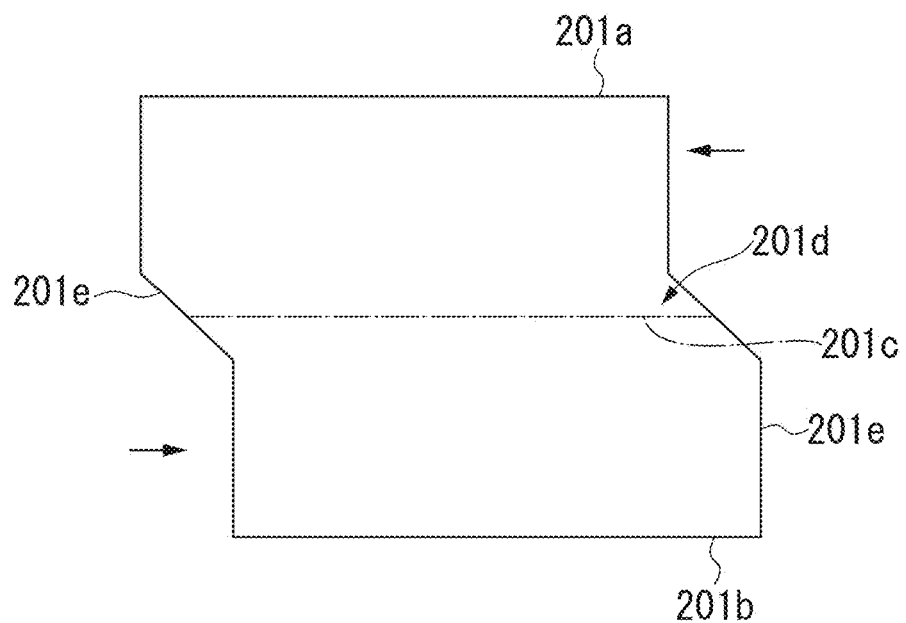
FIG. 10 is a plan view illustrating the first steel sheet to which the shear stress is applied.

Next, as illustrated in FIG. 10, the simple shearing deformation is performed with respect to the first steel sheet 201 by applying the shear stress to make the two regions of the first steel sheet 201 divided by the virtual section 201c shifted from each other in the sheet width direction along the virtual section 201c (that is, to make relative positions of the two regions shifted be on the same surface).

Specifically, in a state where each of the two regions of the first steel sheet 201 divided by the virtual section 201c is bound by the chucking device, the chucking devices are moved to be shifted from each other in the sheet width direction along the virtual section 201c. Accordingly, shearing deformation part 201d is formed near the virtual section 201c. Since the shear stress is applied in the sheet width direction along the virtual section 201c, the sheet thickness at the shearing deformation part 201d does not change compared to that before the stress is applied. Furthermore, there is also a case where the sheet thickness can decrease according to the material, but the largest amount of change in the sheet thickness is at most equal to or less than 1%. Therefore, the local strain is not generated in the test piece similar to a short axial tension test.

However, the shape of sides 201e and 201e which connect the one side 201a and the other side 201b of the first steel sheet 201 to each other, are largely deformed by applying the shear stress to the first steel sheet 201.

The shear strain applied to the first steel sheet 201 by performing shearing process one time is preferably equal to or greater than 0.4. When the applying amount of the shear strain performed one time is set to be equal to or greater than 0.4, the strain amount due to the shearing deformation performed one time does not become extremely small, and the number of steel sheets to be used can be reduced. In the embodiment, the upper limit of the applying amount of the shear strain is not necessarily particularly limited, and the shear stress may be applied until the first steel sheet 201 fractures.

[2-2] First Partial Stress-Strain Curve Data Obtaining Process

In the first partial stress-strain curve data obtaining process, the shear stress and the shear strain which are applied to the first steel sheet 201 in the above-described first shearing process, are measured. In addition, the first partial stress-strain curve data is obtained from a relationship between (1) the shear stress applied to the first steel sheet 201 in the first shearing process, and (2) the total strain amount which is a sum of the shear strain amount which is applied to the first steel sheet 201 in the first shearing process and the first strain amount.

[2-3] Second Shearing Process

In the second shearing process, the shear stress is applied to the second steel sheet 202 which is prepared separately from the first steel sheet 201 by the method similar to the method described in the above [2-1].

The second steel sheet 202 may have the second strain amount different from the first strain amount of the first steel sheet. Therefore, in the embodiment, the first strain amount may be greater or less than the second strain amount.

However, for example, in a case where the second strain amount is greater than the first strain amount, it is preferable that the second strain amount is equal to or less than the strain amount applied to the first plastic sheet in the first shearing process. Accordingly, it is possible to avoid the separation of the strain regions of the first partial stress-strain curve data and the second partial stress-strain curve data from each other, and to obtain the synthesized stress-strain curve data over a wide range of the strain region with high accuracy.

[2-4] Second Partial Stress-Strain Curve Data Obtaining Process

In the second partial stress-strain curve data obtaining process, the shear stress and the shear strain which are applied to the second steel sheet 202 in the above-described second shearing process, are measured. In addition, the second partial stress-strain curve data is obtained from a relationship between (1) the shear stress applied to the second steel sheet 202 in the second shearing process, and (2) the total strain amount which is a sum of the shear strain amount which is applied to the second steel sheet 202 in the second shearing process and the second strain amount.

[2-5] Synthesized Stress-Strain Curve Data Obtaining Process

In the synthesized stress-strain curve data obtaining process, the synthesized stress-strain curve data is obtained at least based on the first partial stress-strain curve data and the second partial stress-strain curve data.

Hereinafter, a method for obtaining one piece of synthesized stress-strain curve data by combining the first partial stress-strain curve data and the second partial stress-strain curve data with each other, will be described with a specific example.

Figure 11:
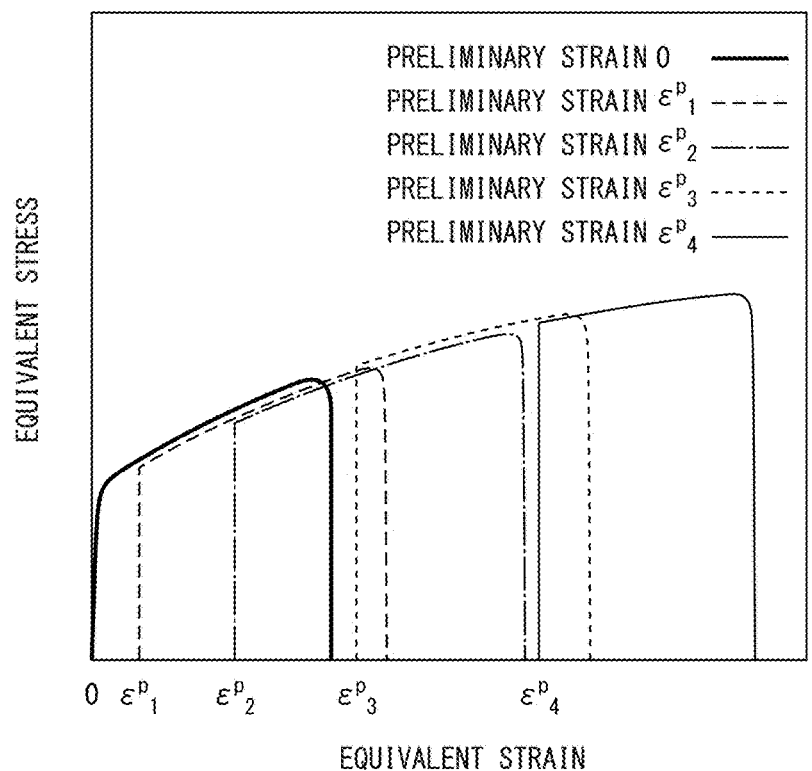
FIG. 11 is a graph illustrating plural pieces of partial stress-strain curve data obtained by the evaluation method of the steel according to the second embodiment of the present invention.

FIG. 11 illustrates five pieces of partial stress-strain curve data (equivalent stress-equivalent plastic strain curve data) obtained by performing the shearing process with respect to five steel sheets having the preliminary strain amounts (0, $\varepsilon^p_1$, $\varepsilon^p_2$, $\varepsilon^p_3$, $\varepsilon^p_4$) different from each other.

As illustrated in FIG. 11, in the partial stress-strain curve of the steel sheet to which the preliminary strain is not applied, the curve from the position at which the equivalent strain is 0 rises, the equivalent stress continues to rise, and after this, the stress returns to 0 as the steel sheet fractures.

In addition, in the partial stress-strain curve of the steel sheet to which the preliminary strain $\varepsilon^p_1$ is applied, the curve rises from the position at which the equivalent strain is $\varepsilon^p_1$, the equivalent stress continues to rise, and after this, the stress returns to 0 as the steel sheet fractures.

Similarly, in the stress-strain curve of the steel sheet to which the preliminary strains $\varepsilon^p_2$ to $\varepsilon^p_4$ are applied, each curve rises from the positions at which the equivalent strains are $\varepsilon^p_2$ to $\varepsilon^p_4$, the equivalent stress continues to rise, and after this, the stress returns to 0 as the steel sheet fractures.

In this manner, in the embodiment, a starting position of the stress-strain curve of the steel sheet to which the preliminary strain $\varepsilon^p$ is applied is the equivalent strain $\varepsilon^p$. In a case where the preliminary strain $\varepsilon^p$ is applied to the steel sheet in advance, the strain applied to the steel sheet becomes a strain obtained by integrating the preliminary strain $\varepsilon^p$ and the shear strain. In addition, by performing the uniaxial shearing test with respect to the steel sheet to which the preliminary strain $\varepsilon^p$ is applied, the stress-strain curve data of the total strain obtained by integrating the preliminary strain and the shear strain, and the equivalent stress which corresponds to the total strain, is obtained. Therefore, as described above, the starting position of the stress-strain curve of the steel sheet to which the preliminary strain $\varepsilon^p$ is applied is the equivalent strain $\varepsilon^p$.

Figure 12:
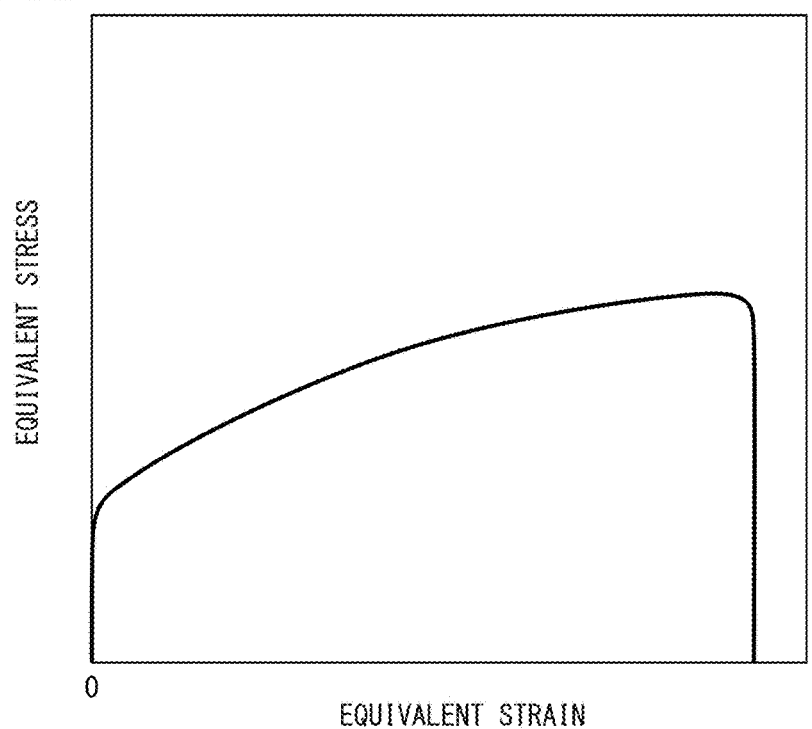
FIG. 12 is a graph illustrating synthesized stress-strain curve data obtained by the evaluation method of the steel according to the second embodiment of the present invention.

Next, as illustrated in FIG. 12, from each of the partial stress-strain curve data, by combining the curve data which is equivalent to the range of the uniform elongation other than the elastic deformation, one piece of synthesized stress-strain curve data is obtained.

At this time, in a case where each curve data substantially overlaps each other, the curve data may be one piece of synthesized stress-strain curve data by combining each curve data while maintaining the overlapping state.

Figure 13:
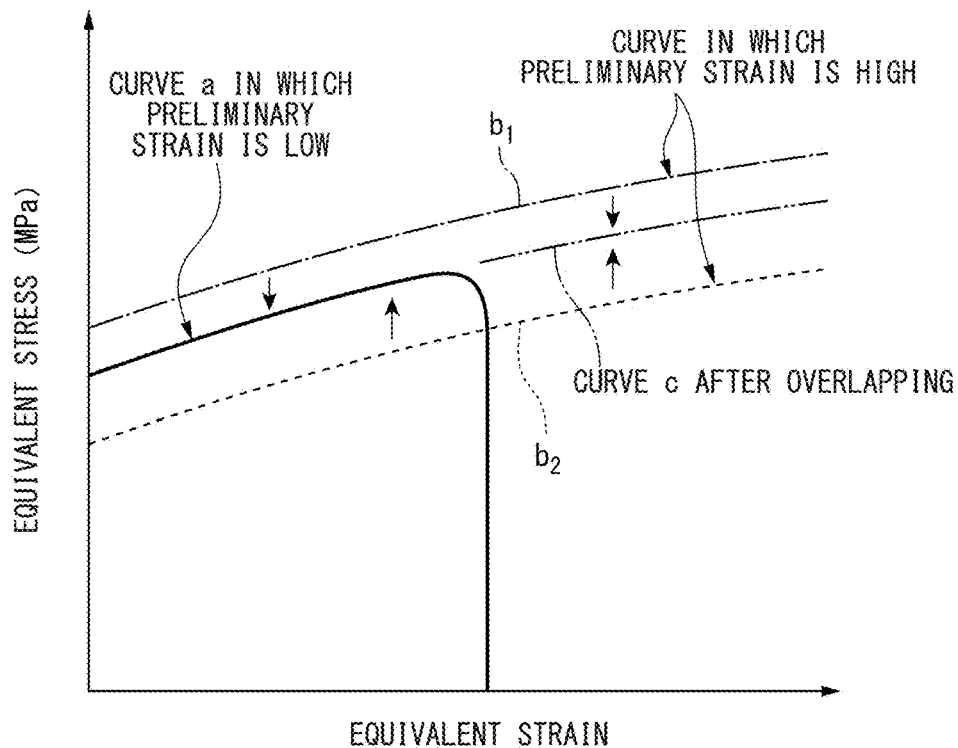
FIG. 13 is a graph illustrating an example of the synthesized stress-strain curve data in the evaluation method of the steel according to the second embodiment of the present invention.

In addition, in a case where a shift occurs while each curve data does not overlap each other, as illustrated in FIG. 13, curve data $b_1$ or $b_2$ of the steel sheet having a high preliminary strain are shifted in the upward-and-downward direction along an axis of the equivalent stress so that the curve data $b_1$ or $b_2$ of the steel sheet having a high preliminary strain overlap curve data a of the steel sheet having a low preliminary strain. For example, as illustrated by one-dot chain line of FIG. 13, in a case where the equivalent stress of the curve data $b_1$ of the steel sheet having a high preliminary strain is high with respect to the curve data a of the steel sheet having a low preliminary strain, the curve data $b_1$ of the steel sheet having a high preliminary strain is shifted downward and overlaps the curve data of the steel sheet having a low preliminary strain. In addition, as illustrated by a dotted line of FIG. 13, in a case where the equivalent stress of the curve data $b_2$ of the steel sheet having a high preliminary strain is low with respect to the curve data a of the steel sheet having a low preliminary strain, the curve data $b_2$ of the steel sheet having a high preliminary strain is shifted upward and overlaps the curve data a of the steel sheet having a low preliminary strain. Curve data c after the overlapping is curve data obtained as the original curve data a and the curve data after the shift overlap each other.

As will be described later, the reason why the above-described handling is possible in the synthesized stress-strain curve data obtaining process, is that an instantaneous work hardening rate obtained from the stress-strain curve data of the steel sheet to which the preliminary strain is applied, and an instantaneous work hardening rate obtained from the stress-strain curve data of the steel sheet to which the preliminary strain is not applied, substantially match each other.

In addition, the reason why the curve data $b_1$ or $b_2$ of the steel sheet having a high preliminary strain are shifted from the curve data a of the steel sheet having a low preliminary strain and the curve data $b_1$ or $b_2$ of the steel sheet having a high preliminary strain, is that the other curve data sequentially overlap each other by considering the stress-strain curve data of the steel sheet having a low preliminary strain as a reference. In addition, the reason why the stress-strain curve data of the steel sheet having a low preliminary strain is a reference, is that there is a case where the equivalent stress is influenced by the preliminary strain in the steel sheet to which the preliminary strain is applied, and the influence is removed as much as possible.

Figure 14:
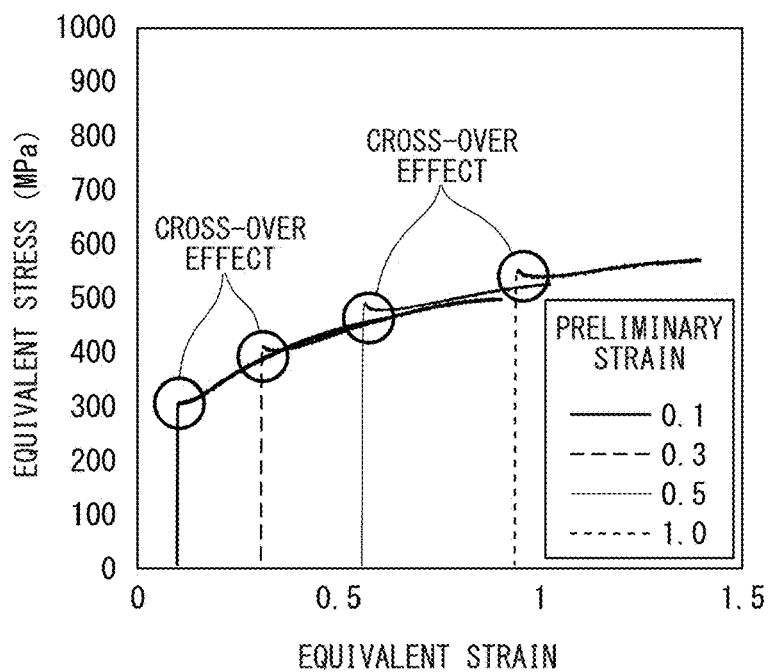
FIG. 14 is a graph illustrating partial stress-strain curve data of each steel obtained by the evaluation method of the steel of the second embodiment of the present invention.

Next, in a case where the simple shearing test is performed with respect to the steel sheet to which the preliminary strain is applied, there is a possibility that a cross-over effect is generated as the preliminary strain and the shear strain are applied. In FIG. 14, the partial stress-strain curve data in which the cross-over effect is generated is illustrated, and the stress-strain curve data illustrated in FIG. 14 is the partial stress-strain curve data of the steel sheet to which 0.1 to 1.0 of preliminary strain is applied, but immediately after the yielding of each curve data, since the curve data indicates a high equivalent stress once, there is a location at which the equivalent stress gradually decreases. The disorder of the curve data is called a cross-over effect, and there is a case where the cross-over effect is generated due to a difference of a path through which the strain is applied. In a case where the cross-over effect is generated, the synthesized stress-strain curve data may be obtained other than the part at which the cross-over effect is generated. The excluded range may be approximately 0.5 times to 1.5 times the preliminary strain $\varepsilon^p$ applied to each steel sheet. In addition, in FIG. 14, the steel sheet to be used is JSC270 material (Japanese Iron and Steel Federation Standard).

Figure 15:
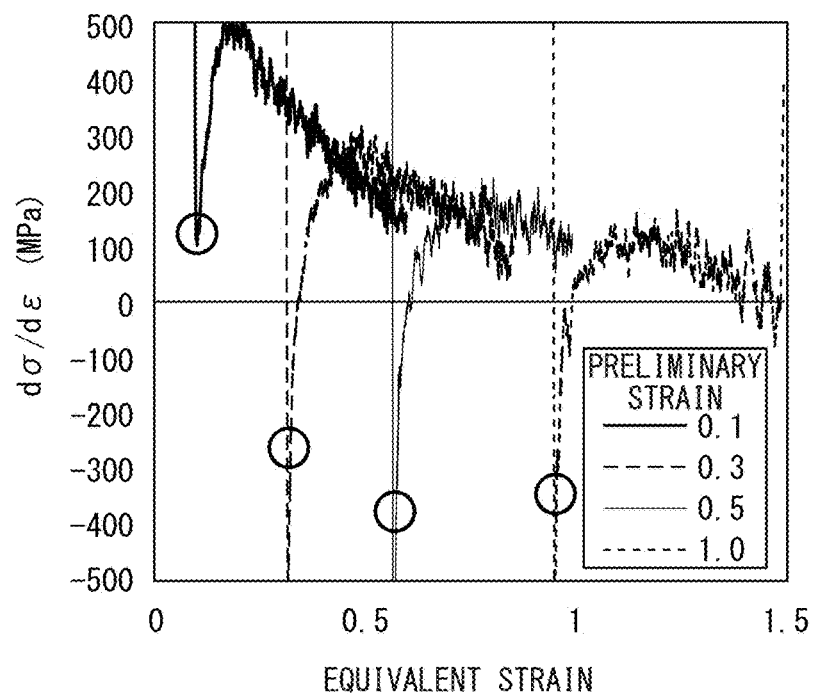
FIG. 15 is a graph illustrating a relationship between an instantaneous work hardening rate obtained from the partial stress-strain curve data illustrated in FIG. 14 and an equivalent plastic strain.

Next, the stress-strain curve data of FIG. 14 was investigated in detail. The investigation result thereof is illustrated in FIG. 15. In FIG. 15, regarding the steel sheet to which the preliminary strains of 0.1, 0.3, 0.5, and 1.0 are respectively applied, the relationship between the instantaneous work hardening rate (dσ/dε) and the equivalent plastic strain is plotted. The instantaneous work hardening rate is the instantaneous gradient of the four partial stress-strain curves illustrated in FIG. 14. As illustrated in FIG. 15, the instantaneous work hardening rate gradually deteriorates as the equivalent strain increase, but it is ascertained that the curve data of the instantaneous work hardening rate of each steel sheet continues to partially overlap each other. In addition, in FIG. 15, the circled part corresponds to the curve data which receives the influence of the cross-over effect illustrated in FIG. 14, and other than the part, it is ascertained that the curve data of the instantaneous work hardening rate of each steel sheet substantially overlap each other. Furthermore, although not illustrated in FIG. 15, the stress-strain curve data of the steel sheet to which the preliminary strains are applied excellently match the stress-strain curve data of the steel sheet to which the preliminary strain was not applied. From the results, it is ascertained that it is possible to reduce the range of the errors to the minimum even when each piece of partial stress-strain curve data of the plurality of steel sheets to which the preliminary strains are gradually applied are integrated with each other in the synthesized stress-strain curve data obtaining process.

As the modification example of the embodiment, after the first shearing process (and/or the second shearing process), a third steel sheet may be obtained by performing the outer form removing process as described in the first embodiment, and third partial stress-strain curve data may be obtained by performing the simple shearing deformation with respect to the third steel sheet.

In the evaluation method of the steel according to the modification example, two steel sheets (the first steel sheet 201 and the second steel sheet 202) having the preliminary strains different from each other are prepared.

Figure 16:
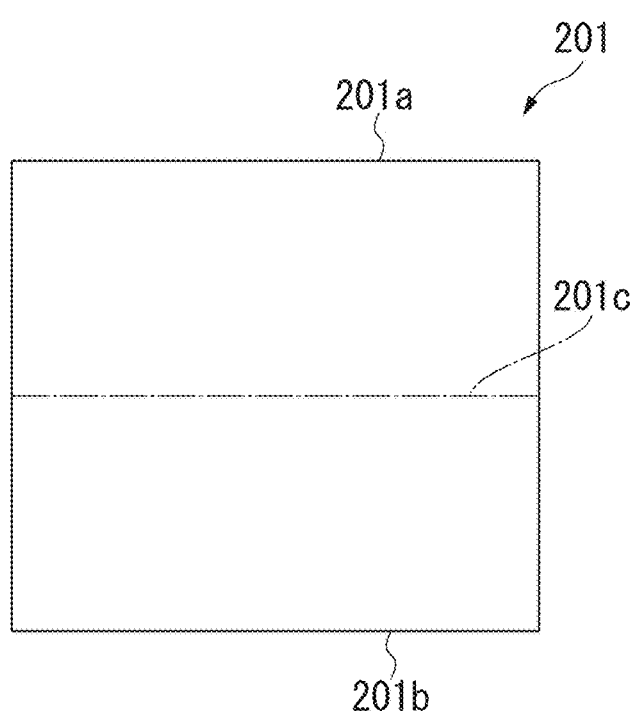
FIG. 16 is a plan view illustrating a first steel sheet which is used in an evaluation method of steel according to a modification example of the second embodiment of the present invention.

Next, as illustrated in FIG. 16, between the one side 201a and the other side 201b of the first steel sheet 201, the virtual section 201c which divides the first steel sheet 201 into two regions is set, and the part including the one side 201a of the first steel sheet 201 and a part including the other side 201b are respectively bound by a fixer which is schematically illustrated.

Figure 17:
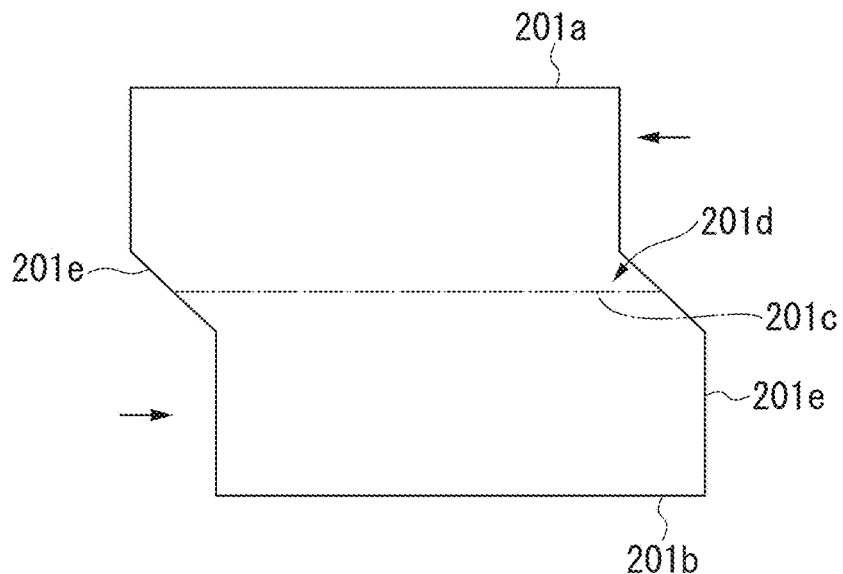
FIG. 17 is a plan view illustrating a first steel sheet to which the shear stress is applied.

Next, as illustrated in FIG. 17, the simple shearing deformation is performed with respect to the first steel sheet 201 by applying the shear stress to make the two regions of the first steel sheet 201 divided by the virtual section 201c shifted from each other in the sheet width direction along the virtual section 201c (that is, to make relative positions of the two regions shifted be on the same surface).

Specifically, in a state where each of the two regions of the first steel sheet 201 divided by the virtual section 201c is bound by the chucking device, the chucking devices are moved to be shifted from each other in the sheet width direction along the virtual section 201c. Accordingly, shearing deformation part 201d is formed near the virtual section 201c. Since the shear stress is applied in the sheet width direction along the virtual section 201c, the sheet thickness at the shearing deformation part 201d does not change compared to that before the stress is applied. Furthermore, there is also a case where the sheet thickness can decrease according to the material, but the largest amount of change in the sheet thickness is at least equal to or greater than 1%. Therefore, the local necking does not occur in the test piece similar to a short axial tension test.

However, the shape of sides 201e and 201e which connect the one side 201a and the other side 201b of the first steel sheet 201 to each other, are largely deformed by applying the shear stress to the first steel sheet 201.

In the modification example, the shear strain applied to the steel sheet by performing shearing process one time is preferably in a range of 0.4 to 1.2, and is more preferably in a range of 0.5 to 1.0. When the applying amount of the shear strain per one instance is set to be equal to or greater than 0.4, the strain amount due to the shearing deformation performed one time does not become extremely small, and the number of repeats of the shearing process and the outer form removing process does not increase. In addition, when the applying amount of the shear strain per one instance is set to be equal to or less than 1.2, it is possible to prevent the fracture of the steel sheet in an early stage.

Figure 18:
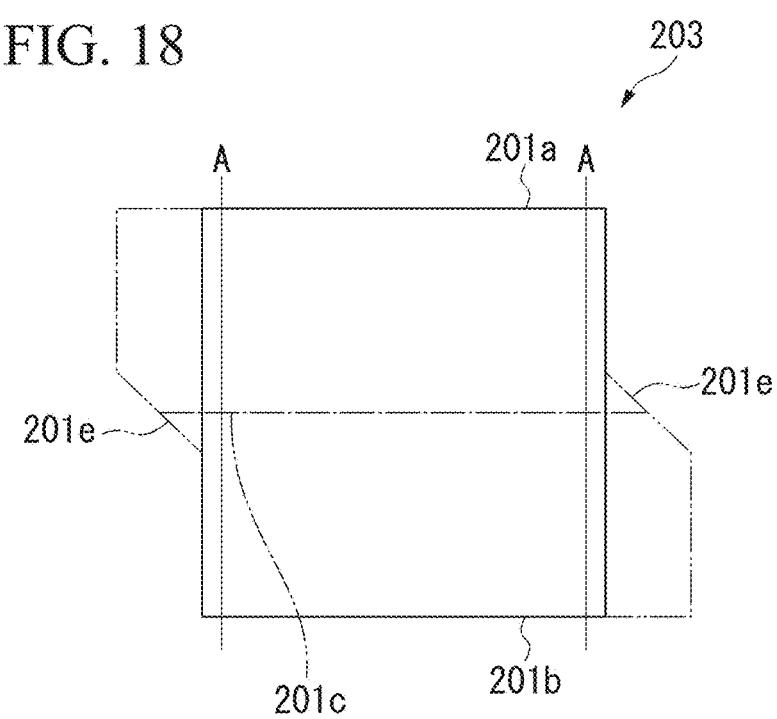
FIG. 18 is a plan view illustrating a third steel sheet obtained by removing the outer form part of the first steel sheet.

In the outer form removing process, as illustrated in FIG. 18, by removing the outer form part deformed by applying the shear stress after unloading the shear stress first, a third steel sheet 203 having a shape of a rectangular flat plane is obtained. Specifically, by cutting off the part including the sides 201e and 201e in the first steel sheet after the first shearing process, the shape of the first steel sheet 201 in a plan view becomes a rectangular shape.

On the sides 201e and 201e which are deformed by applying the shear stress in the first shearing process, there is a possibility that cracks are generated at a location at which the deformation is particularly large. In a state where cracks remain, in the third shearing process which will be described later, there is a concern that the third steel sheet 203 fractures considering cracks as starting points. However, by performing the outer form removing process, since it is possible to obtain the third steel sheet 203 of which cracks which are the starting point of the fracture are removed, it is possible to solve the above-described problem.

Furthermore, in the example illustrated in FIG. 18, among the two regions divided by the virtual section 201c, only one region is respectively removed. However, in the outer form removing process, the outer form part may be removed across the two regions of the first steel sheet 201 along the surface direction perpendicularly intersecting the virtual section 201c and the flat surface of the first steel sheet 201. In other words, the outer form part may be removed along the two lines A in FIG. 18. Accordingly, it is possible to more reliably remove cracks which are the starting points of the fracture.

The simple shearing is performed by a method similar to that of the above-described first shearing process with respect to the third steel sheet 203 obtained by the outer form removing process (third shearing process). In other words, according to the modification example, it is possible to repeat the shearing process plural times during the outer form removing process with respect to one steel sheet. The number of repeats of the process may be one or more. It is not necessary to particularly determine an upper limit of the number of repeats, and the processing may continue until the steel sheet is fractured while applying the shear stress.

Furthermore, since the third steel sheet is obtained after the first shearing process with respect to the first steel sheet, the third steel sheet has the third strain amount 3 greater than that of the first steel sheet. In addition, regarding the third partial stress-strain curve data which will be described later, since the synthesized stress-strain curve data is obtained by synthesizing the first partial stress-strain curve data and the second partial stress-strain curve data, it is preferable that the first strain amount, the second strain amount, and the third strain amount are different from each other.

In addition, by measuring the shear stress and the shear strain which are applied to the third steel sheet 203 in the third shearing process, the third partial stress-strain curve data is obtained from a relationship between (1) the shear stress applied to the third plastic sheet in the third shearing process, and (2) the total strain amount which is a sum of the shear strain amount which is applied to the third plastic sheet in the third shearing process and the third strain amount.

Next, as the synthesized stress-strain curve data obtaining process, one piece of synthesized stress-strain curve data is obtained based on the first partial stress-strain curve data, the second partial stress-strain curve data, and the third partial stress-strain curve data.

The synthesized stress-strain curve data obtaining process at this time, may be performed similar to the synthesized stress-strain curve data obtaining process described above.

Figure 19:
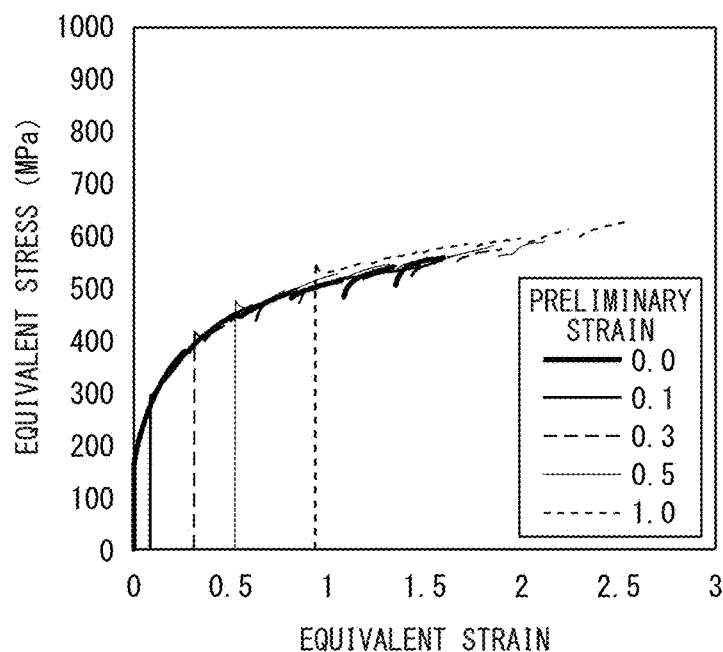
FIG. 19 is a graph illustrating the partial stress-strain curve data of each steel sheet obtained by the evaluation method of the steel according to the second embodiment of the present invention.

In FIG. 19, the partial stress-strain curve data obtained from the plurality of steel sheets is illustrated. In addition, in FIG. 20, a relationship between the instantaneous work hardening rate ($d\sigma/d\varepsilon$) and the equivalent plastic strain is illustrated.

The partial stress-strain curve data illustrated in FIG. 19 is in a state before performing the synthesized stress-strain curve data obtaining process, but it is ascertained that each curve data substantially overlap each other. In addition, as illustrated in FIG. 19, for example, the curve data of the steel sheet to which 1.0 of the preliminary strain is applied is segmented by a plurality of lines, but each of the plurality of lines corresponds to the result of repeating the shearing process with respect to one metal sheet as illustrated in the above-described modification example.

Figure 20:
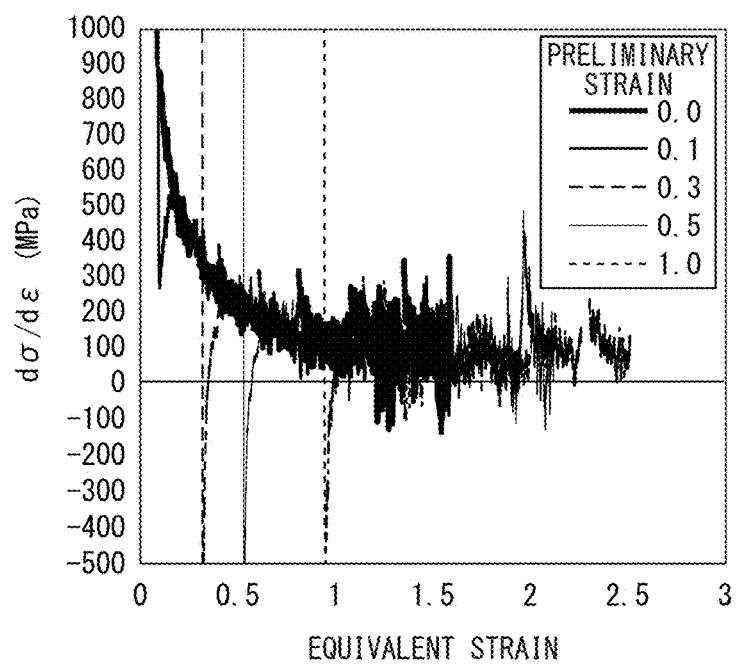
FIG. 20 is a graph illustrating a relationship between an instantaneous work hardening rate obtained from the partial stress-strain curve data illustrated in FIG. 19 and an equivalent plastic strain.

In addition, as illustrated in FIG. 20, the curve data indicating the relationship between the instantaneous work hardening rate ($d\sigma/d\varepsilon$) and the equivalent strain of the steel sheet to which the preliminary strain is applied, and the curve data indicating the relationship between the instantaneous work hardening rate ($d\sigma/d\varepsilon$) and the equivalent strain of the steel sheet to which the preliminary strain is not applied, excellently match each other. As a result, even in a case where the shear stress is repeatedly applied, it is ascertained that the error between the stress-strain curve data of each steel sheet can be reduced to the minimum.

Figure 21:
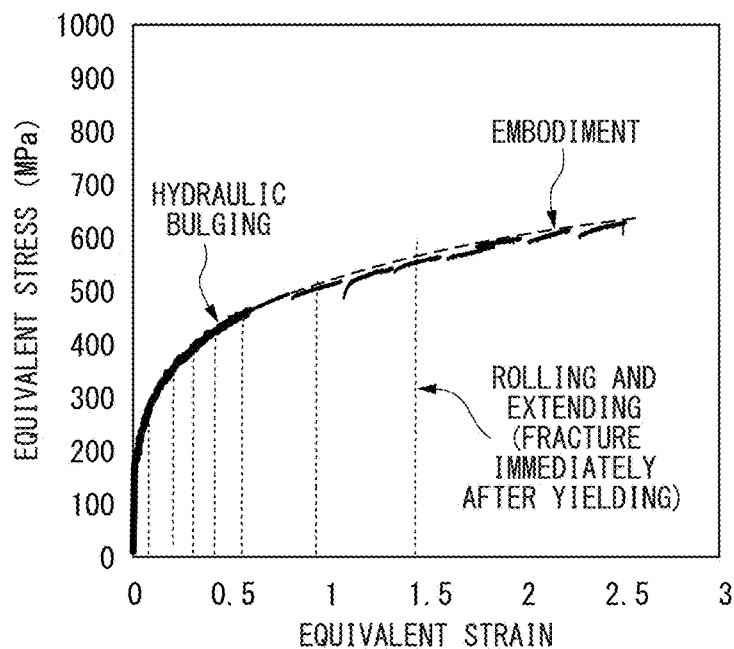
FIG. 21 is a graph which compares the stress-strain curve data obtained by various methods.

In FIG. 21, various types of stress-strain curve data are illustrated. In FIG. 21, (a) the stress-strain curve data obtained by the hydraulic bulging test, (b) the stress-strain curve data obtained by applying the tensile stress to the steel sheet to which the preliminary strain is applied, and (c) the plural pieces of partial stress-strain curve data and synthesized stress-strain curve data which are obtained by the evaluation method of the steel according to the embodiment, are illustrated. It is ascertained that the synthesized stress-strain curve data obtained by the evaluation method of the steel according to the embodiment extends until reaching the strain region wider than that of the stress-strain curve data obtained by the hydraulic bulging test, by performing the measurement by repeating the shearing process. In addition, in a case where the tensile stress is applied to the steel sheet to which the preliminary strain is applied by the rolling, the steel sheet fractures at the time when the tensile stress which corresponds to the yield point is applied. It is predicted that the steel sheet is in a state where the equivalent stress is applied to the steel sheet in advance as the preliminary strain is applied, the local necking immediately occurs in the sheet thickness direction as a tensile load is applied in this state, and the fracture occurs. In a case where the simple shearing test is performed similar to the embodiment, since the local necking does not occur in the sheet direction, the fracture does not immediately occur even in a case of the steel sheet to which the preliminary strain is applied, and each piece of partial stress-strain curve data is obtained.

Figure 22:
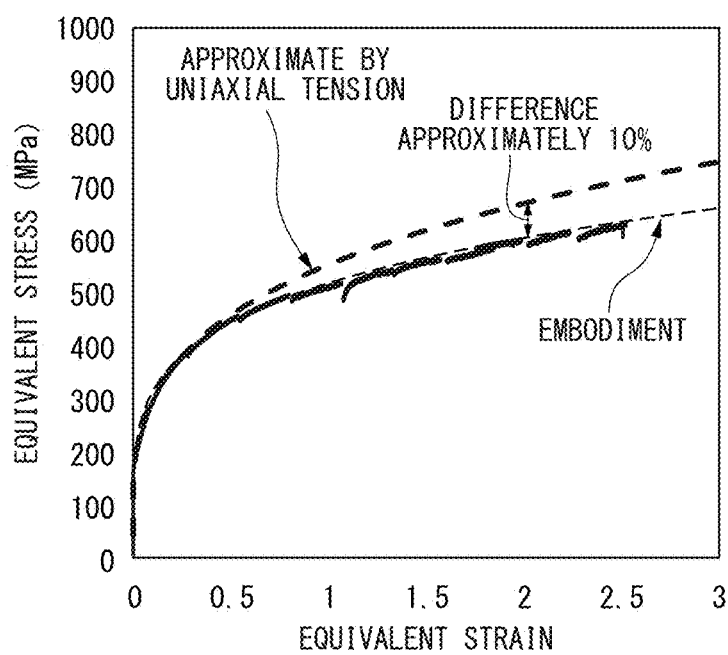
FIG. 22 is a graph which compares the stress-strain curve data obtained by various methods.

In addition, in FIG. 22, (d) the approximate curve data obtained by extrapolating the stress-strain curve data obtained by the uniaxial tension test until reaching the high-strain region, and (e) the plurality of partial stress-strain curve data and synthesized stress-strain curve data which are obtained by the evaluation method of the steel according to the embodiment, are illustrated. It is ascertained that the synthesized stress-strain curve data obtained by the evaluation method of the steel according to the embodiment has a difference which is approximately 10% when the equivalent strain is in the vicinity of 2.0 with respect to the approximate curve data.

As described above, according to the evaluation method of the steel according to the embodiment, since one piece of synthesized stress-strain curve data is obtained based on the partial stress-strain curve data of each steel sheet by respectively performing the simple shearing deformation with respect to the plurality of steel sheets having the strain amounts different from each other, and by obtaining the partial stress-strain curve data for each steel sheet, it is possible to obtain the stress-strain curve data until reaching the high-strain region by the actual measurement.

In addition, in the synthesized stress-strain curve data obtaining process, from the stress-strain curve data other than the elastic deformation of each steel sheet, by combining the curve data of the strain region other than the part which receives the influence of the cross-over effect, it is possible to obtain the synthesized stress-strain curve data with a small amount of error.

Furthermore, similar to the above-described modification example, in a case where the shearing process is performed plural times with respect to one steel sheet during the outer form removing process, the plural pieces of stress-strain curve data having the strain regions different from each other are obtained from one steel sheet. As a result, since the strain region which can be covered by one steel sheet is enlarged, for example, by two or three steel sheets, it is possible to obtain the synthesized stress-strain curve data which covers a wide range of the strain region.

(Third Embodiment)

In the evaluation method of the steel according to the embodiment, by employing a new approximation instead of the approximation similar to the Swift equation of the related art with respect to one piece of partial stress-strain curve data obtained by the shearing process described in the first embodiment and the second embodiment, highly accurate synthesized stress-strain curve data is obtained.

Furthermore, highly accurate synthesized stress-strain curve data may be obtained by employing new approximation to the plural pieces of partial stress-strain curve data obtained by the shearing process described in the first embodiment and the second embodiment.

Hereinafter, the evaluation method of the steel according to the third embodiment of the present invention will be described with reference to FIGS. 23 to 28.

The evaluation method of the steel according to the embodiment includes: [3-1] a first shearing process of performing the shearing deformation with respect to a first steel sheet 301; [3-2] a partial stress-strain curve data obtaining process of obtaining first partial stress-strain curve data from a measurement result of the first shearing process; and [3-3] a stress-strain curve data obtaining process of obtaining stress-strain curve data based on the first partial stress-strain curve data. Hereinafter, each process will be described in detail.

[3-1] First Shearing Process

Figure 23:
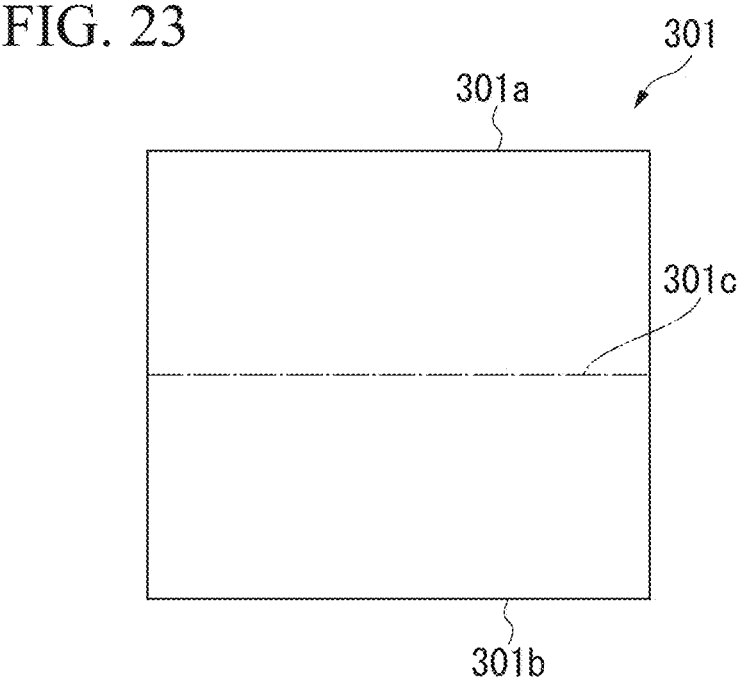
FIG. 23 is a plan view illustrating a first steel sheet which is used in an evaluation method of steel according to a third embodiment of the present invention.

As illustrated in FIG. 23, the first steel sheet 301 is a steel sheet having a shape of a rectangular flat surface. The preliminary strain may be applied to the first steel sheet 301 as necessary. In other words, the first steel sheet 301 has a first strain amount (which may include 0).

As illustrated in FIG. 23, between one side 301a and the other side 301b of the first steel sheet 301, a virtual section 301c which divides the first steel sheet 301 into two regions is set. The virtual section 301c is set perpendicularly to the surface of the first steel sheet 301. In addition, in a case where the virtual section 301c is a boundary, a part including the one side 301a of the first steel sheet 301 and a part including the other side 301b are respectively bound by a fixer which is schematically illustrated. As the fixer, a chucking device which grabs and fixes the first steel sheet 301 can be illustrated as an example.

Figure 24:
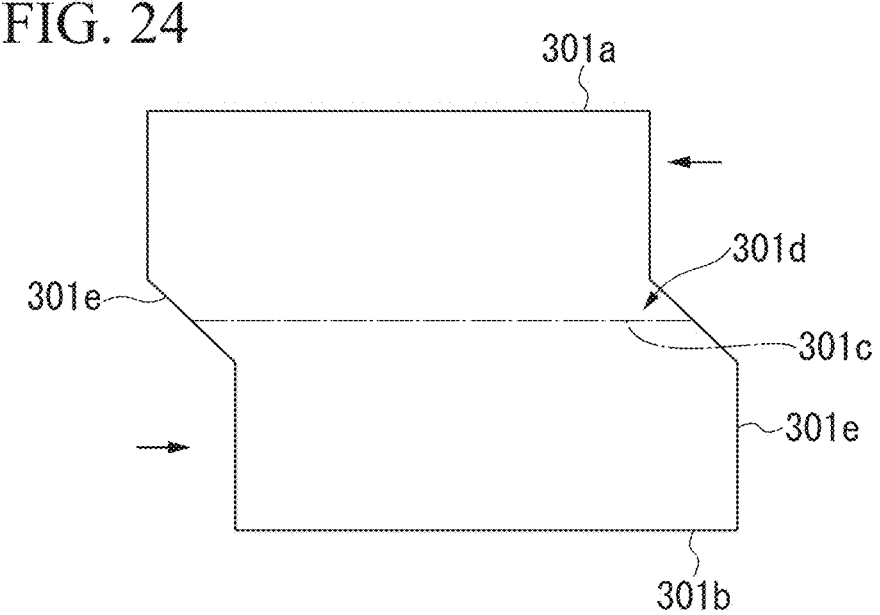
FIG. 24 is a plan view illustrating a first steel sheet to which the shear stress is applied.

Next, as illustrated in FIG. 24, the simple shearing deformation is performed with respect to the first steel sheet 301 by applying the shear stress to make the two regions of the first steel sheet 301 divided by the virtual section 301c shifted from each other in the sheet width direction along the virtual section 301c (that is, to make relative positions of the two regions shifted be on the same surface).

Specifically, in a state where each of the two regions of the first steel sheet 301 divided by the virtual section 301c is bound by the chucking device, the chucking devices are moved to be shifted from each other in the sheet width direction along the virtual section 301c. Accordingly, shearing deformation part 301d is formed near the virtual section 301c. Since the shear stress is applied in the sheet width direction along the virtual section 301c, the sheet thickness at the shearing deformation part 301d does not change compared to that before the stress is applied. Furthermore, there is also a case where the sheet thickness can decrease according to the material, but the largest amount of change in the sheet thickness is at least equal to or greater than 1%. Therefore, the local necking does not occur in the test piece similar to a short axial tension test.

However, the shape of sides 301e and 301e which connect the one side 301a and the other side 301b of the first steel sheet 301 to each other, are largely deformed by applying the shear stress to the first steel sheet 301. The shearing process may continue until the steel sheet is fractured in the middle of applying the shear stress.

[3-2] First Partial Stress-Strain Curve Data Obtaining Process

In the first partial stress-strain curve data obtaining process, the shear stress and the shear strain which are applied to the first steel sheet 301 in the above-described first shearing process, are measured. In addition, the first partial stress-strain curve data is obtained from a relationship between (1) the shear stress applied to the first steel sheet 301 in the first shearing process, and (2) the total strain amount which is a sum of the shear strain amount which is applied to the first steel sheet 301 in the first shearing process and the first strain amount.

[3-3] Stress-Strain Curve Data Obtaining Process

In the stress-strain curve data obtaining process, the stress-strain curve data is obtained based on at least the first partial stress-strain curve data and the second partial stress-strain curve data.

Specifically, the stress-strain curve data is obtained by approximating the first partial stress-strain curve data by the relational equation expressed by the following equation (3).

$$\sigma = K(\varepsilon^p + a)^m \quad (3)$$

$$m = n^* + 1/\{b(\varepsilon^p + c)\} \quad (4)$$

here, in equation (3), σ is an equivalent stress, K (MPa) and a are material factors of the plastic material, $\varepsilon^p$ is an equivalent plastic strain, and m is as illustrated in the above-described equation (4), and in equation (4), n* is a convergence value of a work hardening coefficient, b is a parameter indicating the rate of convergence of the work hardening coefficient, and c is a parameter indicating the rate of development of the work hardening coefficient.

Figure 25:
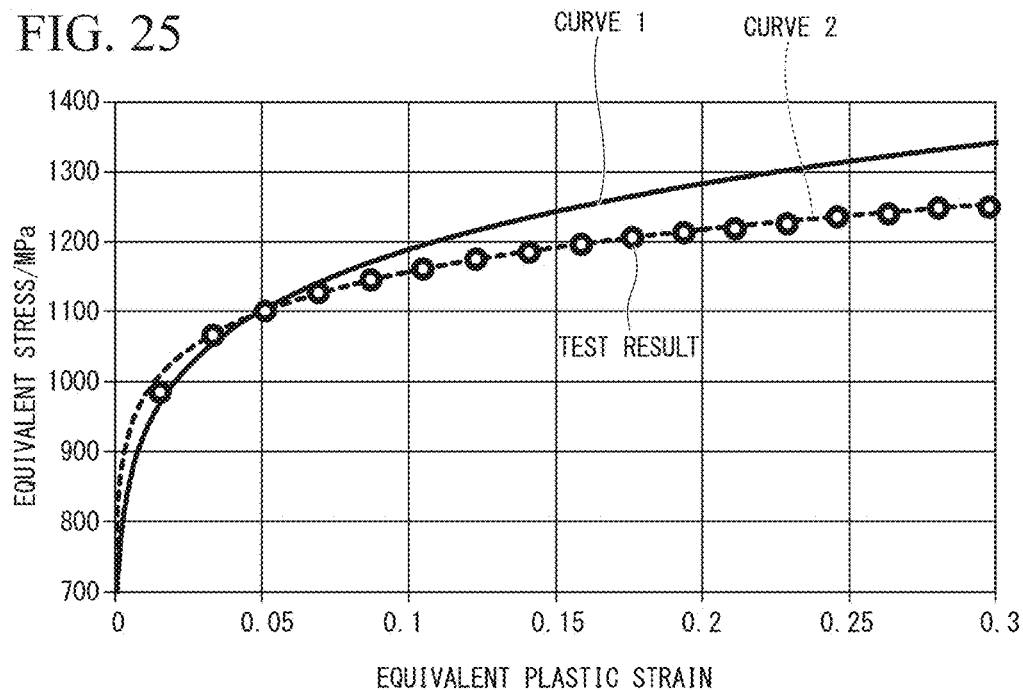
FIG. 25 is a graph illustrating partial stress-strain curve data obtained by a simple shearing deformation test, and equivalent stress-equivalent plastic strain curve data approximated by the Swift equation.

As an example, in FIG. 25, the relationship between the equivalent stress (shear stress) and the equivalent plastic strain (shear strain) which are obtained from the result of the simple shearing test of the embodiment is illustrated by white circled marks. In this example, the preliminary strain amount of the first steel sheet 301 is 0.

In addition, in FIG. 25, the equivalent stress-equivalent plastic strain curve data approximated by the Swift equation is also illustrated. From the curve data illustrated in FIG. 25, curve data 1 is obtained by approximating the equivalent stress-equivalent plastic strain curve data by the Swift equation illustrated in the following equation (5), from the relationship between the equivalent stress and the equivalent plastic strain which are obtained by the uniaxial tension test of the related art. In addition, curve data 2 illustrated in FIG. 25 is obtained by approximating the equivalent stress-equivalent plastic strain curve data by the Swift equation illustrated in the following equation (5) from the relationship between the equivalent stress and the equivalent plastic strain which are obtained by the simple shearing test method of the embodiment. In addition, in the uniaxial tension test of the related art, measurement is possible from the yielding until reaching the uniform elongation, and in the simple shearing test method, measurement is possible to the strain region of a range which exceeds the uniform elongation of the stress-strain curve data in the uniaxial tension test of the related art. The steel supplied for the test is a steel sheet in which the tensile strength is 1051 MPa, the yield strength is 750 MPa, and the sheet thickness is 1.6 mm.

$$\sigma = \alpha(\varepsilon^p + \beta)^n \tag{5}$$

Here, in equation (5), σ is an equivalent stress, α and β are constants determined for each steel sheet, $\varepsilon^p$ is a plastic strain, and n is a work hardening coefficient.

As illustrated in FIG. 25, it is ascertained that approximation accuracy of the curve data 1 becomes lower compared to that of the curve data 2.

Figure 26:
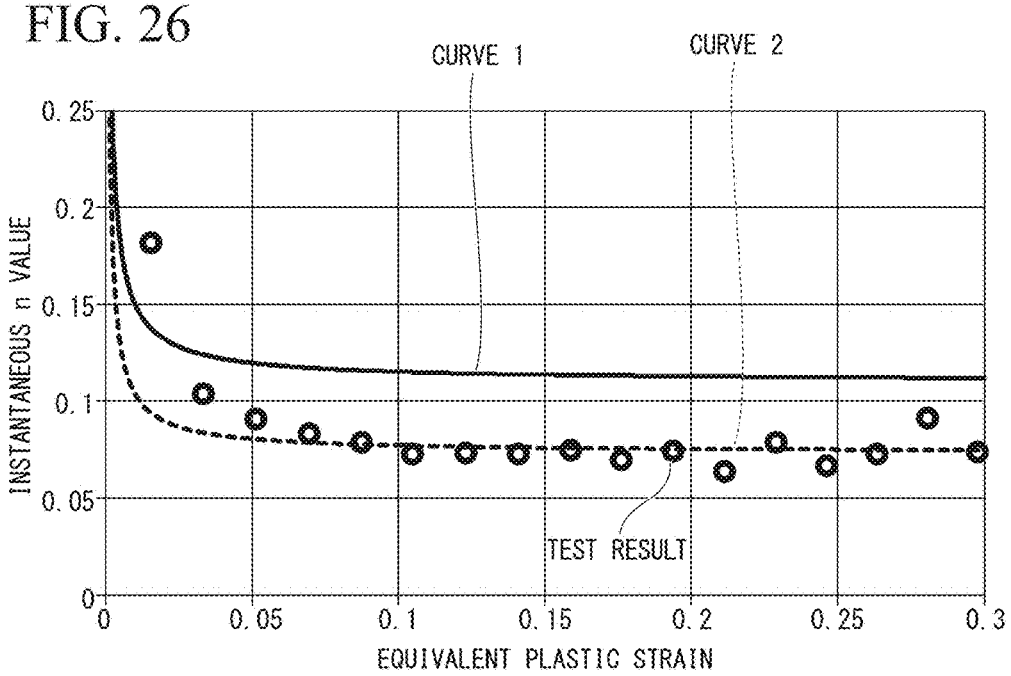
FIG. 26 is a graph illustrating a relationship between an instantaneous n value obtained from the partial stress-strain curve data illustrated in FIG. 25 and an equivalent plastic strain.

The reason of the separation of the two pieces of curve data was investigated, and a relationship between the instantaneous n value and the plastic strain was investigated. The result thereof is illustrated in FIG. 26. The instantaneous n value is an instantaneous gradient in the stress-strain curve data (the curve data 1 and the curve data 2) illustrated in FIG. 25. Specifically, the stress-strain curve data is plotted by both logarithmic graphs, and is collinear approximated in each section of 0.025 of increment of the equivalent strain, and the inclination thereof is the instantaneous n value. The result thereof is illustrated in FIG. 26. As illustrated in FIG. 26, in the actual steel sheet, the instantaneous n value decreases until the strain amount becomes approximately 0.1, and after this, is converged to approximately 0.07 to 0.08.

In addition, the instantaneous n value obtained base on the curve data 1 decreases until the strain amount becomes approximately 0.05, and the instantaneous n value is converged to approximately 0.12 in the strain region in which the strain amount exceeds 0.05. In this manner, in the curve data 1, the behavior of decrease in the instantaneous n value in the low-strain region causes substantial separation from an actually measured value, and the instantaneous n value itself in the high-strain region is substantially separated from the actually measured value.

Meanwhile, the instantaneous n value obtained based on the curve data 2 decreases until the strain amount becomes approximately 0.025, and is converged to a constant value of 0.07 to 0.08 when the strain amount exceeds 0.025. In the curve data 2, in the high-strain region, the separation between the instantaneous n value and the actually measured value is small, but the behavior of decrease in the instantaneous n value in the low-strain region causes substantial separation from the actually measured value similar to the curve data 1.

As illustrated in the curve data 1 and curve data 2 of FIGS. 25 and 26, since the Swift equation is an equation on the assumption that an n value is converged to the constant value in the low-strain region, it is not possible to reproduce a change in the n value of the actual steel sheet. Since the n value indicating the work hardenability of the material becomes an important factor not only in the strain distribution or the stress distribution in the forming analysis, but also in the forming defect prediction of wrinkles or cracks, the approximation accuracy thereof substantially influences the analysis result.

Here, after close investigation, the inventors found that the following equation (6) excellently matches the actual stress-strain curve data. The equation is an approximate which is obtained by analyzing highly accurate synthesized stress-strain curve data obtained by the evaluation method of the steel according to the above-described first embodiment and the second embodiment.

$$\sigma = K(\varepsilon^p + a)^m \tag{6}$$

$$m = n^* + 1/\{b(\varepsilon^p + c)\} \tag{7}$$

Here, in equation (6), σ is an equivalent stress, K(MPa) and a are material factors of each steel sheet, $\varepsilon^p$ is an equivalent plastic strain, and m is as illustrated in the above-described equation (7), and in the equation (7), n* is a convergence value of a work hardening coefficient, b is a parameter indicating the rate of convergence of the work hardening coefficient, and c is a parameter indicating the rate of development of the work hardening coefficient. b is in a range of −5000 to 5000, and c is in a range of 0 to less than 1.

The above-described equation (6) is obtained by investigating that the instantaneous n value changes together with the development of the strain in the low-strain region and a new function of the work hardening similar to the convergence to the constant value is created in the high-strain region.

First, as a form of the function, an index type from an experimental factor which is called convergence to the constant value in the high-strain region, may be employed, and the Swift equation which is widely used currently is used as a base.

Next, regarding the instantaneous n value in the low-strain region, in order to indicate a high value immediately after the yielding by the test result, and to indicate a tendency of gradually or rapidly decreasing and becoming converged together with the development of the strain, an index part of the Swift equation is a sum of a constant term and a strain dependence term (a term having the equivalent plastic strain as a denominator) which decreases together with the development of the strain.

Coefficients of the strain dependence term are two including b indicating the rate of convergence of the instantaneous n value, and c indicating the rate of the development of the instantaneous n value. The coefficient b is in a range of −5000 to 5000, and more preferably in a range of −1000 to 4000. A reference numeral of the coefficient b can reproduce the behavior of the instantaneous n value which is often found in a material which is excellent in extension in a case of being positive. In addition, the reference numeral of the coefficient b can reproduce the behavior of the instantaneous n value which is often found in a material which is excellent in hole expanding properties in a case of being negative. In addition, the coefficient c is in a range of 0<c<1, and more preferably in a range of 0.01≤c<0.05. By inserting the coefficient c thereto, a role of preventing the m value from becoming infinite in a case where the equivalent plastic strain is 0, and the calculation in the value analysis from being impossible, is also achieved.

Figure 27:
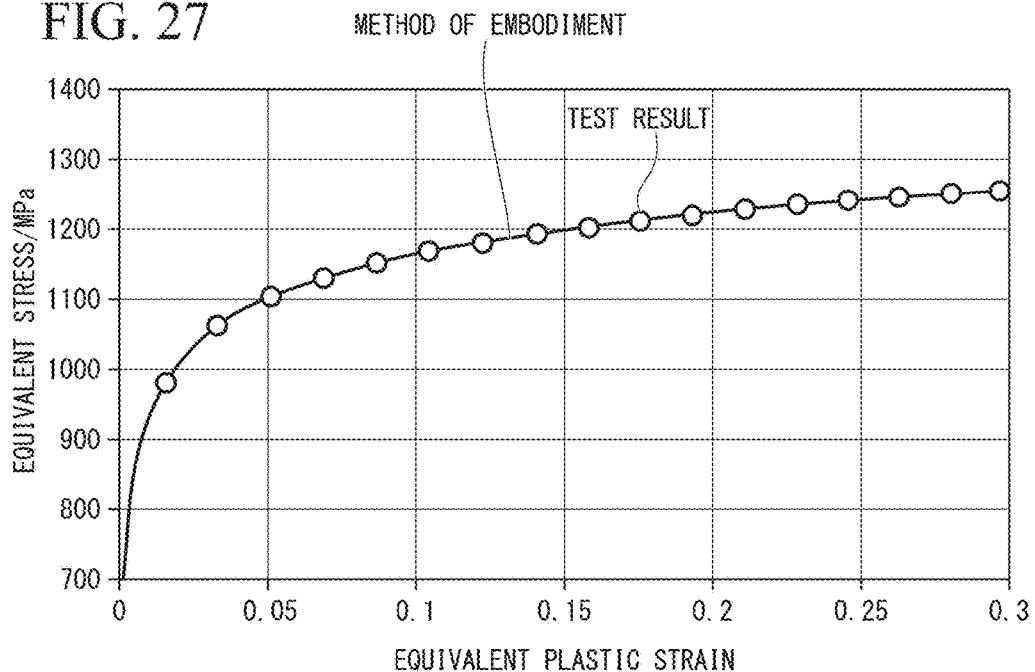
FIG. 27 is a graph illustrating synthesized stress-strain curve data obtained by the evaluation method of the steel according to the third embodiment of the present invention.
Figure 28:
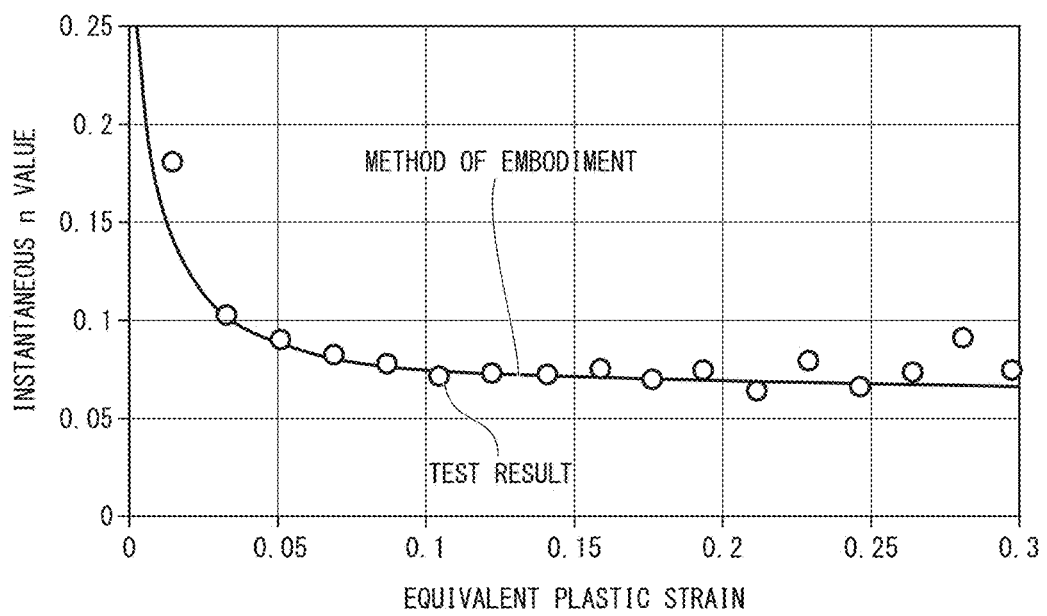
FIG. 28 is a graph illustrating a relationship between the instantaneous n value obtained from the synthesized stress-strain curve data illustrated in FIG. 27 and an equivalent plastic strain.

Based on the above-described idea, the equation (6) measures the stress-strain curve data by the evaluation method of the steel of the embodiment with respect to actually 40 or more types of steel sheets, and is derived from the measurement result, and in a range where the plastic strain amount is from 0 to 1.0 or more, excellently matches the result with the actually measured value of the stress-strain curve data. In FIG. 27, curve data which is drawn based on the equation (6) is illustrated, and in FIG. 28, curve data indicating the relationship between the instantaneous n value and the strain which is drawn based on the equation (6) is illustrated. It is ascertained that both of the curve data excellently match the result obtained by the simple shearing test. In addition, the test result of FIGS. 27 and 28 are the same as the measurement result of the steel sheet in FIGS. 25 and 26.

Furthermore, in the embodiment, the stress-strain curve data is obtained by employing the approximation to one piece of partial stress-strain curve data. However, the synthesized stress-strain curve data may be obtained by employing the approximation to the plural pieces of partial stress-strain curve data obtained by the method described in the above-described first embodiment and the second embodiment.

Next, a method of using the synthesized stress-strain curve data obtained by the evaluation method of the steel described in the first embodiment to the third embodiment of the present invention in the analysis of the deformation processing, will be described based on the fourth embodiment to the sixth embodiment.

(Fourth Embodiment)

In the analysis of the deformation processing of the steel, a finite element method is used. In the finite element method of the related art, there are many cases where a parameter of a work hardening law, such as the Swift equation, is used. However, the inventors made it apparent that the Swift equation is not employed in the actually measured value particularly in the high-strain region. Here, in the embodiment, the synthesized stress-strain curve data obtained by the above-described evaluation method of the steel is utilized in the finite element method.

Specifically, for example, a computer provided with an analyzer which obtains the strain distribution and the maximum strain in a case where the press forming is performed with respect to the steel sheet by a finite element method may be used, the measured value of the synthesized stress-strain curve data obtained by the above-described evaluation method of the steel may be input to the analyzer of the computer, and the analyzer may be operated by the computer. The analyzer provided in the computer is realized as each function of a central processing unit (CPU) of the computer for performing each of steps 101 to 106 illustrated in FIG. 29

Hereinafter, as an analyzing method of the steel deformation processing of the embodiment, an order of analyzing the strain distribution when the hole expanding processing which is one type of the press forming is performed with respect to the steel sheet, by the finite element method, will be described.

Figure 30:
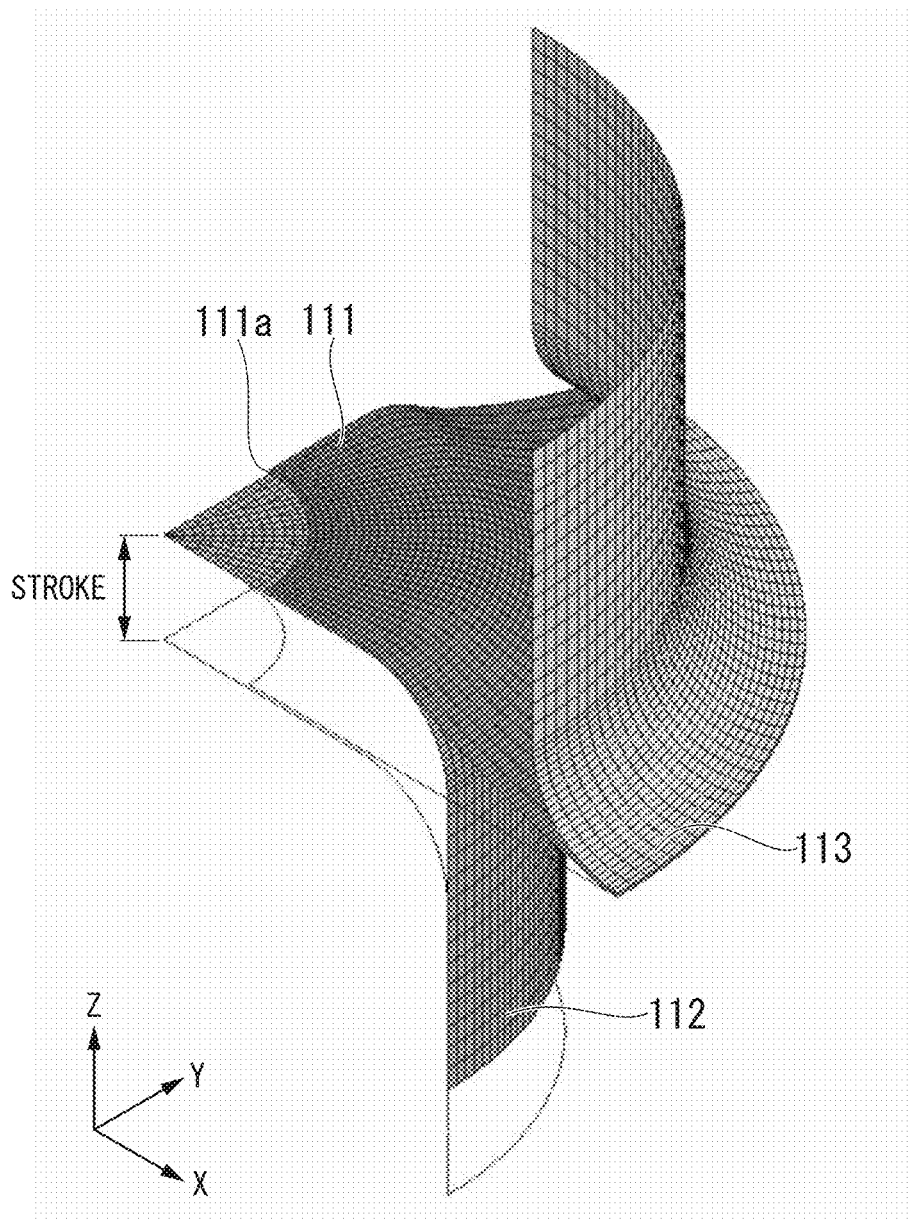
FIG. 30 is a partial perspective view illustrating a processing method of a cylindrical hole expanding processing.

First, a process of the hole expanding processing will be described with reference to FIG. 30. FIG. 30 is a perspective view after cutting out ¼ of the entire steel sheet, the punch, and the die. As illustrated in FIG. 30, a blank 111 (steel sheet) provided with a hole 111a is prepared, a punch 112 for expanding a hole is disposed below the steel sheet 111, and a die 113 is disposed on the steel sheet 111. In addition, by raising the punch 112, the hole expanding processing which widens the hole 111a provided in the steel sheet 111 is performed.

A case where cracks are not generated at an edge part of the hole of the steel sheet after the hole expanding processing, is not considered as a forming defect, and a case where cracks are generated, is considered as a forming defect. When excessive stress is partially concentrated with respect to the edge part of the hole, a possibility of generation of cracks increases. Here, by the forming analysis which uses the finite element method, the distribution of the stress of the edge part of the hole of the steel sheet after the hole expanding processing is predicted.

Figure 29:
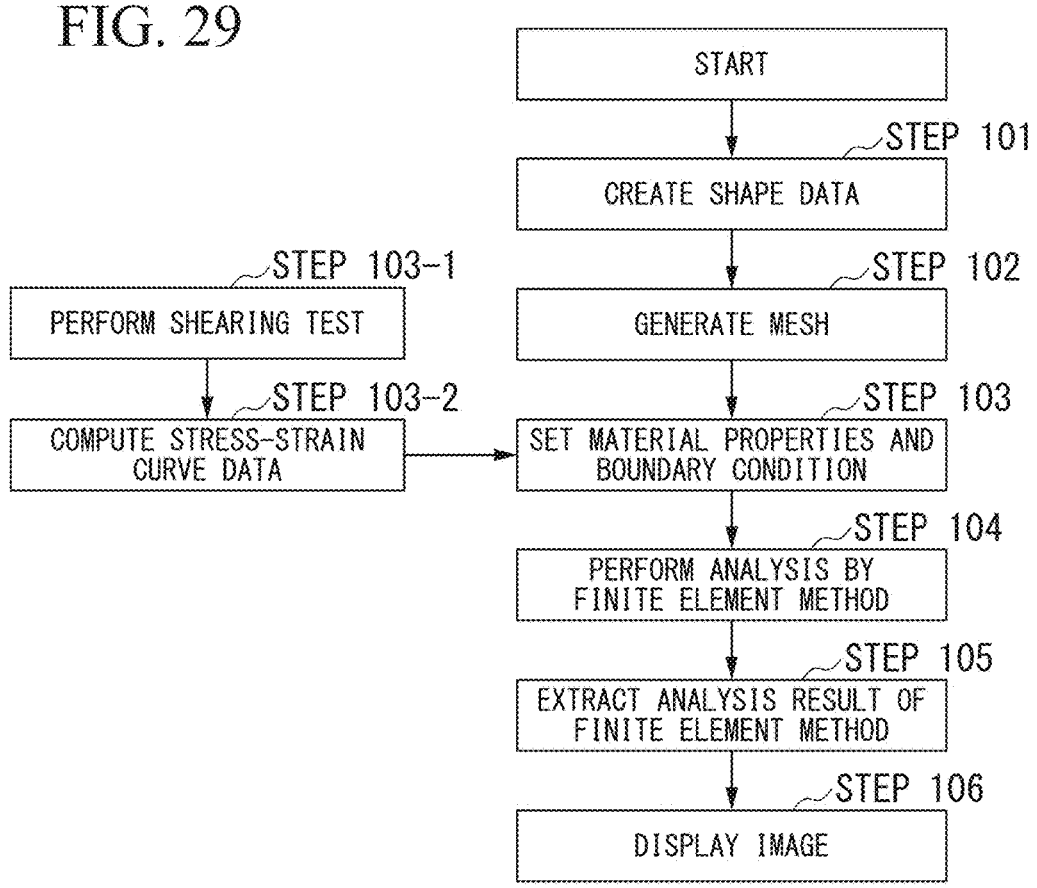
FIG. 29 is a flow chart illustrating an evaluation method of deformation processing of steel according to a fourth embodiment of the present invention.

As illustrated in FIG. 29, first, in step 101, shape data of the steel sheet which is the analysis target is created.

Next, in step 102, a mesh is generated by dividing the shape data created in step 101 by the finite element. The generation of the mesh can use, for example, a mesh generation program included in an analysis package or the like of a commercially available finite element method. A shape of the finite element may be any of a triangle and a quadrangle. The size of the finite element may be appropriately set in accordance with the size, the shape, the thickness, and the boundary condition of the steel sheet which is the analysis target.

Next, in step 103, the material properties and the boundary condition of the steel sheet are set. In addition, in the step 103, the synthesized stress-strain curve data obtained by the simple shearing test is input.

The material properties are the sheet thickness or elastic modulus of the steel sheet 111 which is the blank, and may use physical properties of the steel sheet 111 as it is. For example, in a case of the steel sheet in which the tensile strength is 600 MPa, the yield strength is 400 MPa, and the sheet thickness is 1.6 mm is used, each of the physical properties is input.

In addition, the boundary conditions are a binding position, a load position, and a load weight of the steel sheet 111 when the cylindrical hole expanding processing is performed with respect to the steel sheet 111. When the cylindrical hole expanding processing is performed, the binding position may be a position at which the steel sheet 111 is bound by the punch 112 and the die 113. In addition, in a case where the load is applied to the steel sheet 111 by the cylindrical hole expanding processing, the load position may be a position at which the load is transmitted to the steel sheet 111.

In addition, the synthesized stress-strain curve data input in step 103 is used in the finite element analysis instead of the parameter of the work hardening law, such as the Swift equation of the related art. The synthesized stress-strain curve is obtained by sequentially performing step 103-1 of performing the simple shearing test, and step 103-2 of creating the synthesized stress-strain curve data based on the result of the simple shearing test. In each of steps 103-1 and 103-2, the above-described evaluation method of the steel may be performed.

Next, in step 104, the finite element analysis is performed based on the mesh, the material properties, and the boundary condition. For example, as analysis software, NASTRAN manufactured by MSC Software Corporation, or ABAQUS/STANDARD manufactured by Dassault Systemes S. A., which is a multi-purpose structure analysis finite element method code of a static implicit method, can be used.

Figure 31A:
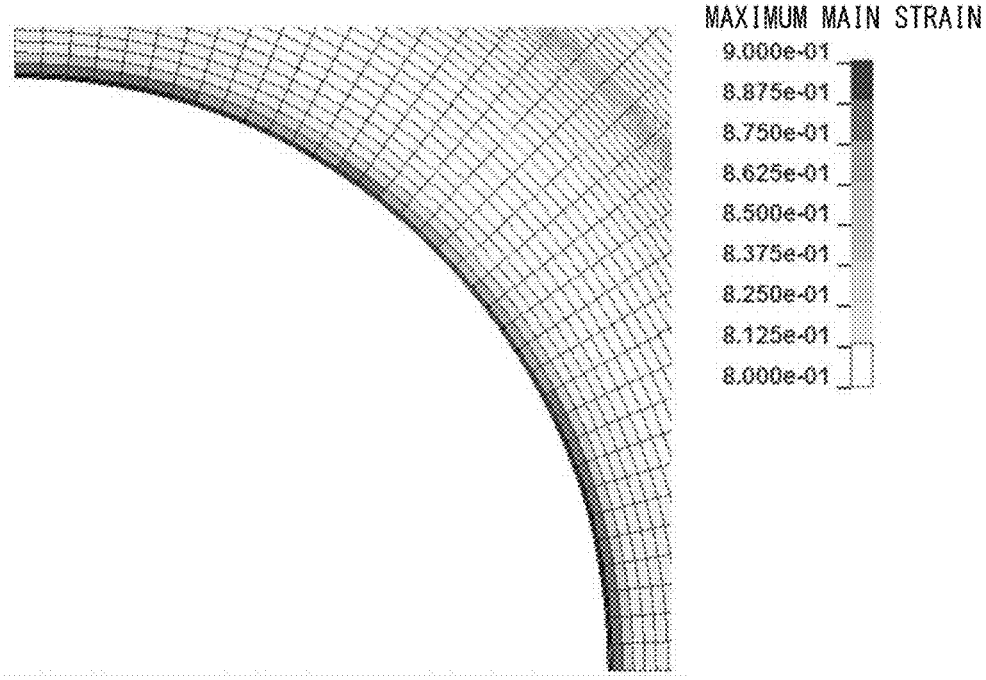
FIG. 31A is an outline view illustrating a result of performing analysis of the cylindrical hole expanding processing of the steel sheet based on a material parameter obtained by the Swift equation of the related art.
Figure 31B:
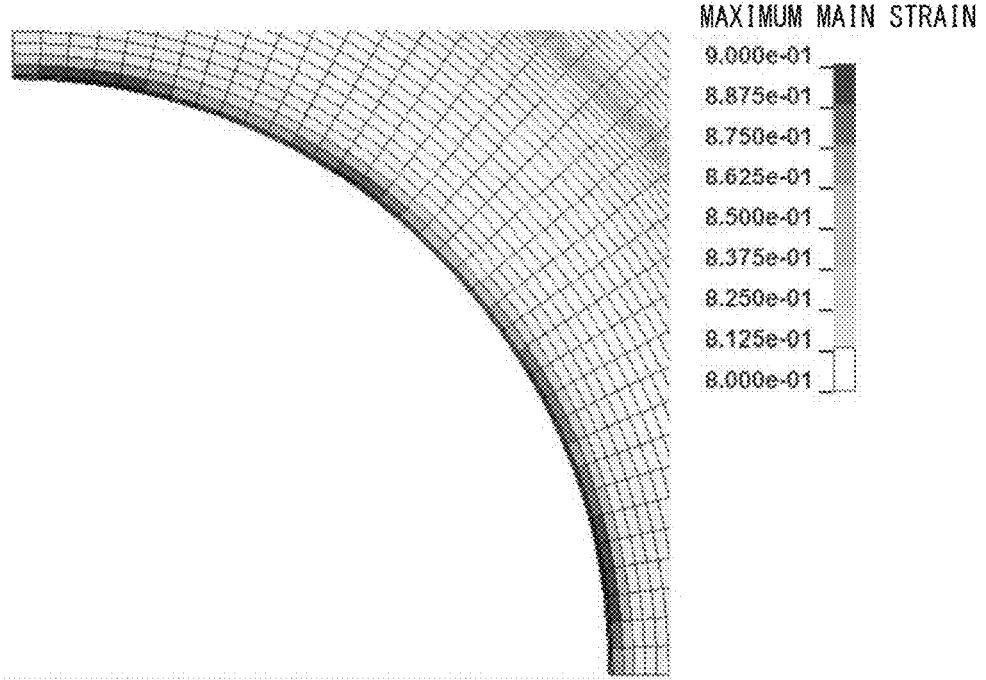
FIG. 31B is an outline view illustrating a result of performing analysis of the cylindrical hole expanding processing of the steel sheet based on the synthesized stress-strain curve data obtained by the evaluation method of the steel according to the first embodiment of the present invention.

Next, in step 105, the obtained result in the finite element analysis is extracted. In addition, in step 106, the analysis result is output as a screen to an output device of the computer. In FIGS. 31A and 31B, an example of the analysis result is illustrated.

Figure 32:
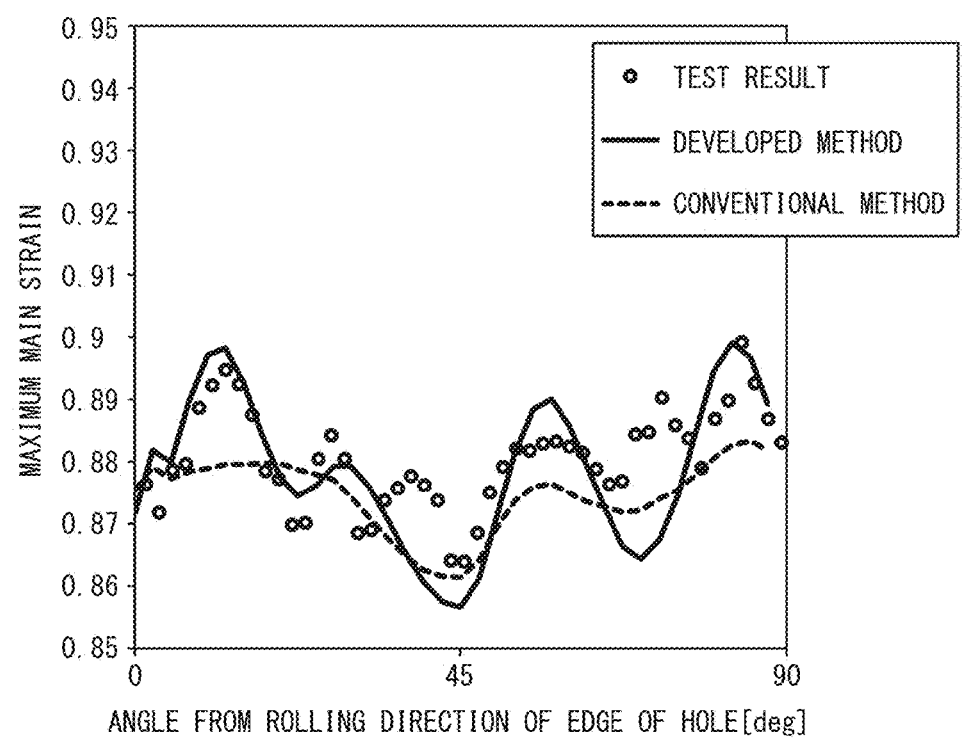
FIG. 32 is a graph illustrating a distribution of the maximum strain amount at an edge of a hole after the cylindrical hole expanding processing of the steel sheet.

In FIGS. 31A and 31B, a cylindrical hole expanding analysis result of the steel sheet is illustrated. FIG. 31A is an outline view illustrating a result of performing the analysis of the cylindrical hole expanding processing of the steel sheet based on a material parameter obtained by the Swift equation of the related art. In addition, FIG. 31B is an outline view illustrating a result of performing the analysis of the cylindrical hole expanding processing of the steel sheet based on the synthesized stress-strain curve data obtained by the evaluation method of the steel according to the first embodiment of the present invention. FIGS. 31A and 31B illustrate the strain distribution when reaching a stroke amount by which cracks are generated by actually performing the hole expanding processing. In addition, in FIG. 32, the distribution of the maximum strain amount at the edge of the hole after the cylindrical hole expanding processing of the steel sheet, is illustrated.

In FIG. 31A, the maximum strain amount at a part of the edge of the hole indicates approximately 0.88, and the strain amount distribution is also relatively uniform. Meanwhile, in FIG. 31B, the maximum strain amount at the part of the edge of the hole indicates approximately 0.90, and the strain locally increases.

According to FIG. 31A, since the strain amount is distributed to be relatively small and uniform, it is determined that a risk of generation of cracks is low. According to FIG. 31B, it is determined that there is a risk of generation of cracks at a location at which the strain is locally high. Here, the cylindrical hole expanding processing is actually performed by using the above-described steel sheet, and then, cracks are generated in the vicinity of the edge of the hole, and are as illustrated in FIG. 31B. Therefore, it is ascertained that the evaluation method of the deformation processing of the steel according to the embodiment can be performed as the forming analysis with higher accuracy compared to the related art.

In this manner, according to the evaluation method of the steel deformation processing according to the embodiment, since the synthesized stress-strain curve data is obtained from the shear stress and shear strain which are obtained by the above-described evaluation method of the steel, and the maximum strain distribution in a case where the cylindrical hole expanding processing is performed by inputting the obtained synthesized stress-strain curve data to the computer and by performing the press forming with respect to the steel sheet, is obtained, it is possible to correctly detect the generation of cracks of the steel sheet in the press forming. In addition, the evaluation method of the deformation processing of the steel according to the embodiment can also be employed in the sheet forging or the cold forging as the deformation processing, and for example, it is possible to correctly predict the forming load required for the processing.

(Fifth Embodiment)

In the forming analysis of the deformation processing, the finite element method is used. In the finite element method of the related art, there are many cases where the parameter of the work hardening law, such as the Swift equation, is used, or where the curve data which is approximated by extrapolating the stress-strain curve data obtained by the simple tension test until reaching the high-strain region. However, it is ascertained that the approximate curve data or the extrapolated curve data which are obtained by the Swift equation have a large error particularly in the high-strain region. Here, in the embodiment, the synthesized stress-strain curve data obtained by the above-described evaluation method of the steel is used in the finite element method.

Specifically, for example, the computer provided with the analyzer which performs the forming analysis of the steel deformation processing by the finite element method may be used, the synthesized stress-strain curve data obtained by the above-described evaluation method of the steel may be input to the analyzer of the computer, and the analyzer may be operated by the computer. The analyzer provided in the computer is realized as each function of the central processing unit (CPU) of the computer for performing each of steps 201 to 206 illustrated in FIGS. 33A, 33B, and 33C. In addition, as the forming analysis performed by the computer, at least one of the strain distribution, the maximum strain, and the forming load of the steel in a case where the deformation processing is performed with respect to the steel, can be obtained.

Hereinafter, as an application example of an analyzing method of the steel deformation processing of the embodiment, a forming analyzing method when creating a cub-like member from a steel sheet which is circular when viewed in a plan view by the sheet forging, will be described.

Figure 33A:
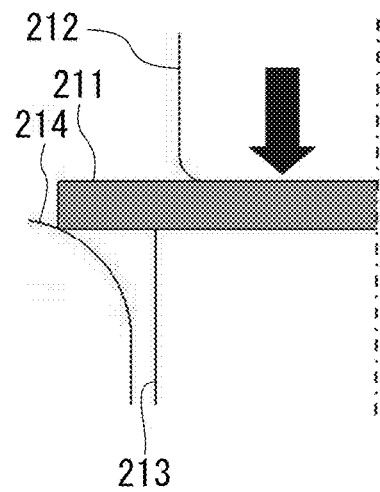
FIG. 33A is a first process view illustrating sheet forging of the steel sheet.
Figure 33B:
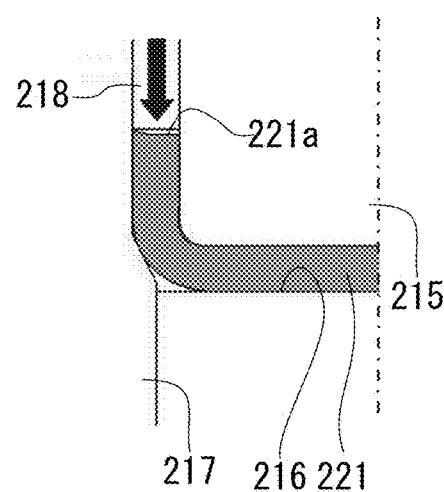
FIG. 33B is a second process view illustrating the sheet forging of the steel sheet.
Figure 33C:
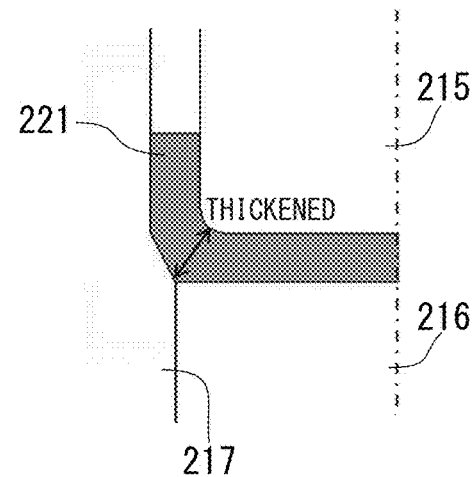
FIG. 33C is a third process view illustrating the sheet forging of the steel sheet.

First, a process of the sheet forging will be described with reference to FIGS. 33A, 33B, and 33C. One-dot chain lines of FIGS. 33A, 33B, and 33C are symmetric axes. First, as illustrated in FIG. 33A, a steel sheet 211 which is punched in a circular shape is prepared, and the steel sheet 211 is nipped and fixed between a cylindrical punch 212 and a cushion 213. In addition, on the periphery of cushion 213, a die 214 having an opening into which the punch 212 can infiltrate is disposed.

In addition, while maintaining a state where the die 214 is fixed, the press forming is performed by lowering the punch 212 toward the opening of the die 214, and the steel sheet 211 is formed into the cup 221. In the steel sheet 211, the bending processing is partially performed by the punch 212 and the die 214. The sheet thickness of the bending-processed part decreases from the sheet thickness of the original steel sheet.

Next, as illustrated in FIG. 33B, the punch 212 is replaced with a pad 215, the cushion 213 is replaced with another die 216, and further, the die 214 is replaced with another cushion 217. In addition, the pad 215 is inserted into a cup 221, the die 216 is pressed from a lower side of the cup 221, and further, the cushion 217 is disposed on an outer circumferential surface of the cup 221. In addition, another punch 218 is pressed against an end part 221a of the cup 221, and upsetting processing is performed.

In FIG. 33C, a state after the forming is completed is illustrated. A part which is thinned by the initial press forming, is thickened by the upsetting processing. In this manner, by the sheet forging, the cup of which a bent part is thickened is obtained.

Here, in obtaining the cup which does not have a forming defect, a balance of the forming load of the cushion 217 and the punch 218 is important. When the forming load of the cushion 217 is insufficient, cushion 217 is pushed to a lower part of the die 216, and as a result, the shape of the cup 221 is collapsed. In addition, when the forming load of the punch 218 is insufficient, the upsetting processing is not performed sufficiently, and the thickness does not sufficiently increase. Here, in order to obtain an appropriate balance of the forming load of the cushion 217 and the punch 218, the forming analysis is performed by the finite element method.

Figure 34:
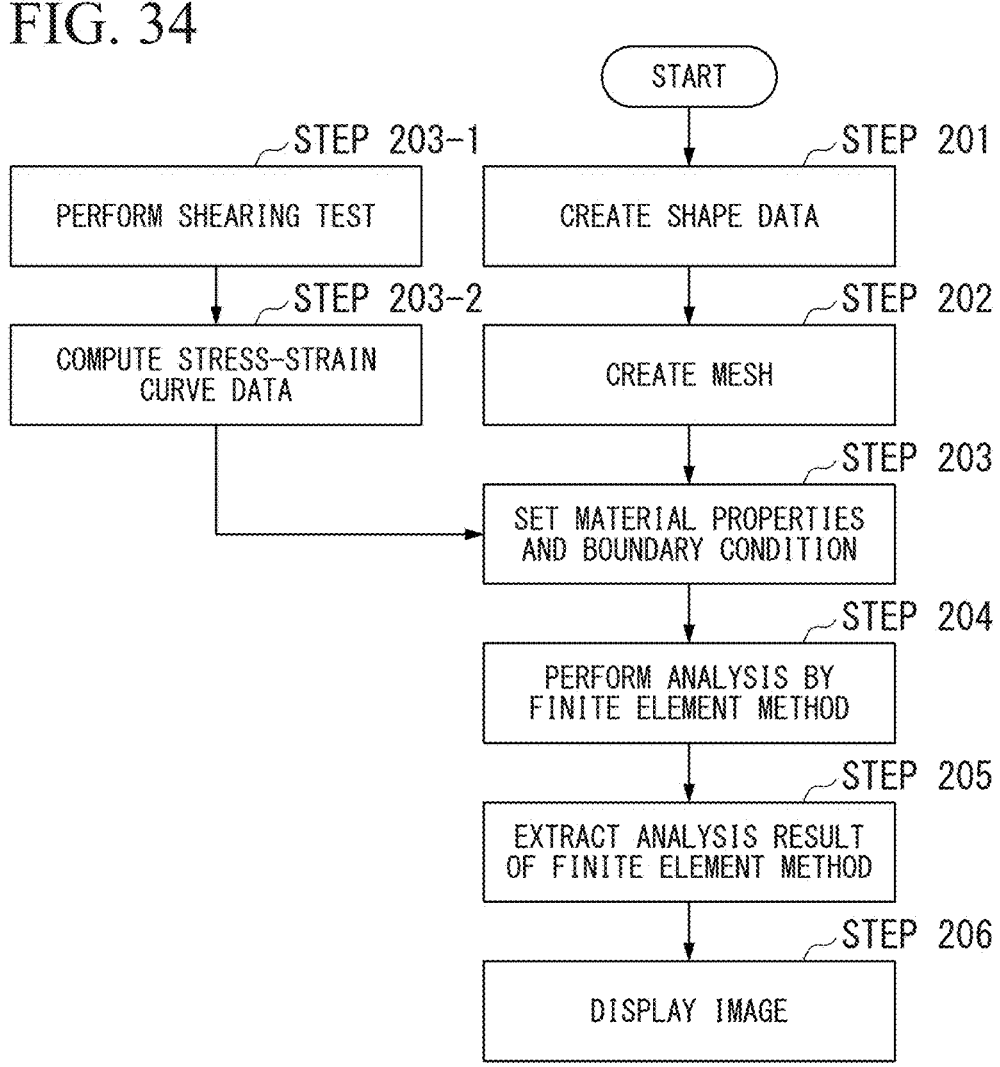
FIG. 34 is a flow view illustrating an evaluation method of deformation processing of steel according to a fifth embodiment of the present invention.

In the forming analysis, as illustrated in FIG. 34, first, in step 201, the shape data of the steel sheet which is circular when viewed in a plan view that is an analysis target, is created.

Next, in step 202, a mesh is generated by dividing the shape data created in step 201 by the finite element. The generation of the mesh can use, for example, a mesh generation program included in an analysis package or the like of a commercially available finite element method. A shape of the finite element may be any of a triangle and a quadrangle. The size of the finite element may be appropriately set in accordance with the size, the shape, the sheet thickness, and the boundary condition of the steel sheet which is the analysis target.

Next, in step 203, the material properties and the boundary condition of the steel sheet are set. In addition, in the step 203, the synthesized stress-strain curve data obtained by the simple shearing test is input.

The material properties are the sheet thickness or elastic modulus of the steel sheet, and may use the physical properties of the steel sheet as it is.

In addition, the boundary conditions are a binding position, a load position, and a load weight of the steel sheet when the sheet forging is performed with respect to the steel sheet. When the sheet forging is performed, the binding position may be a position at which the steel sheet is bound by the pad 215, the die 216, the cushion 217, and the punch 218. In addition, in a case where the load is applied to the steel sheet from the cushion 217 and the punch 218, the load position may be a position at which the load is transmitted to the steel sheet.

In addition, the synthesized stress-strain curve data input in step 203 is used in the finite element analysis. The synthesized stress-strain curve data is obtained by sequentially performing the shearing process (step 203-1) of performing the simple shearing test, and the synthesized stress-strain curve data obtaining process (step 203-2) of creating the synthesized stress-strain curve data based on the result of the simple shearing test. In each of steps 203-1 and 203-2, the above-described evaluation method of the steel may be performed.

Next, in step 204, the finite element analysis is performed based on the mesh, the material properties, and the boundary condition. For example, as analysis software, NASTRAN which is a multi-purpose structure analysis finite element method code of a static implicit method, can be used.

Figure 35A:
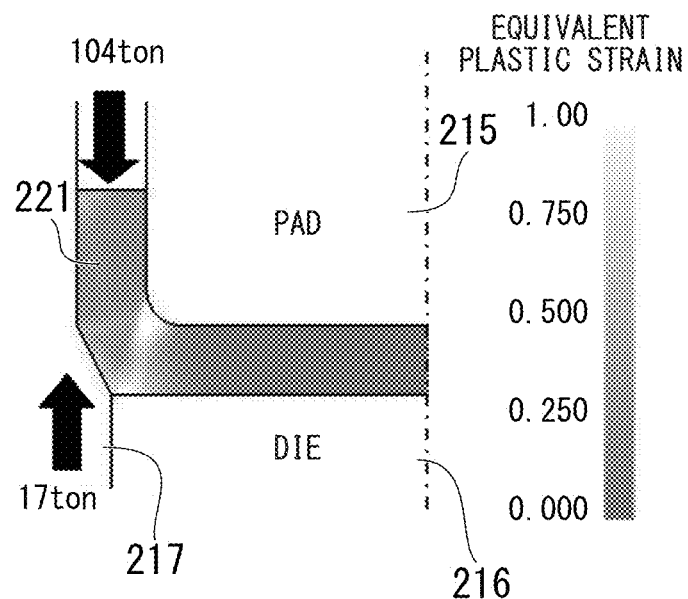
FIG. 35A is a view illustrating a result of performing analysis of the sheet forging of the steel sheet based on the synthesized stress-strain curve data obtained by the evaluation method of the steel according to the second embodiment of the present invention.
Figure 35B:
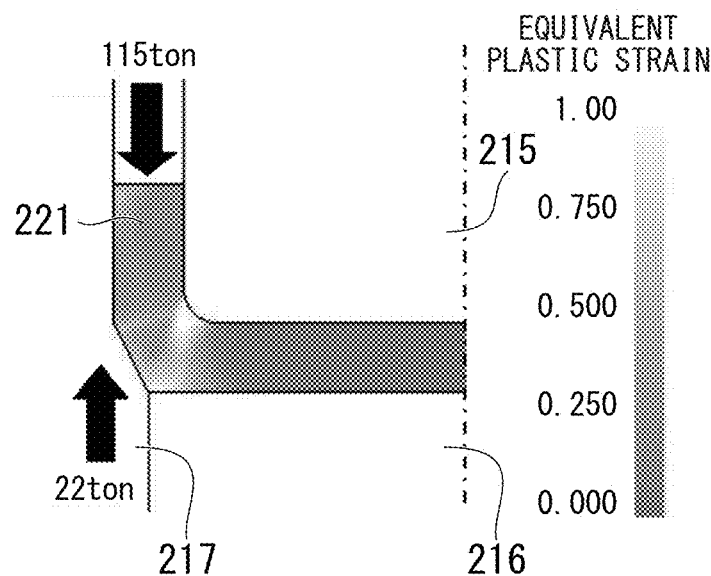
FIG. 35B is a view illustrating a result of performing analysis of the sheet forging of the steel sheet based on the stress-strain curve data obtained by the uniaxial tension test.

Next, in step 205, the obtained result in the finite element analysis is extracted. In addition, in step 206, the analysis result is output as a screen to the output device of the computer. In FIGS. 35A and 35B, an example of the analysis result is illustrated.

In FIGS. 35A and 35B, the analysis result in a case where the cup 221 is formed by the sheet forging is illustrated.

FIG. 35A illustrates a result of performing the forming analysis based on the synthesized stress-strain curve data illustrated in FIG. 22 obtained by the evaluation method of the steel according to the second embodiment of the present invention, and illustrates a cushion load when the upsetting processing is performed, a punch load, and an equivalent plastic strain distribution of the cup section.

In addition, FIG. 35B is a view illustrating a result of performing the forming analysis based on the approximate curve data illustrated in FIG. 22 created based on the stress-strain curve data obtained by the uniaxial tension test, and similar to FIG. 35A, illustrates the cushion load when the upsetting processing is performed, the punch load, and a stress distribution of the cup section.

In FIG. 35A, it is ascertained that the punch load is 104 tons and the cushion load is 17 tons. Meanwhile, in FIG. 35B, the punch load is 115 tons and the cushion load is 22 tons, and any one of the punch load and the cushion load is a higher value compared to that of FIG. 35A. In addition, when focusing on the strain distribution of the cup section, it is ascertained that the region in which the equivalent plastic strain is equal or greater than 1 is smaller in FIG. 35A than that of FIG. 35B. When performing the steel forging based on the analysis result of FIG. 35B, since the cushion load and the punch load are excessive, there is a possibility of causing any forming defect.

In this manner, according to the evaluation method of the deformation processing of the steel according to the embodiment, by inputting the measured data of the synthesized stress-strain curve data obtained by the above-described evaluation method of the steel to the computer, it is possible to enhance the accuracy of the forming analysis in a case where the deformation processing is performed with respect to the steel sheet with a high strain amount. For example, in a case where the press forming is employed as the deformation processing, it is possible to predict the strain distribution and the maximum strain of the steel sheet in the press forming, and to correctly detect the generation of cracks. In addition, in a case where the sheet forging or the cold forging is employed as the deformation processing, by obtaining the forming load amount to the steel due to the forming tool, it is possible to predict the forming load required for the processing.

(Sixth Embodiment)

In the analysis of the deformation processing, the finite element method is used. In the finite element method of the related art, there are many cases where the parameter of the work hardening law, such as the Swift equation is used. However, the inventors made it apparent that the stress-strain curve data until reaching the strain region in which the uniform elongation is exceeded from the yield point and the instantaneous n value cannot be reproduced by the Swift equation. Here, in the embodiment, the forming analysis of the steel deformation processing is performed by utilizing the equation (6) described in the third embodiment in the finite element method.

Specifically, for example, the computer provided with the analyzer which obtains the maximum strain distribution in a case where the press forming is performed with respect to the steel sheet by the finite element method may be used, K(MPa), a, b, c, and n* which are material parameters in the above-described equation (6) may be input to the analyzer of the computer, and the analyzer may be operated by the computer. The analyzer provided in the computer is realized as each function of the central processing unit (CPU) of the computer for performing each of steps 301 to 306 illustrated in FIG. 36. In addition, in the computer, a computer program which executes a step of inputting the relational equation expressed by the equation (6) as a relational approximation between the equivalent plastic stress and the plastic strain, and a step of obtaining the strain distribution and the maximum strain in a case where the deformation processing is performed with respect to the steel sheet by the finite element method based on the relational equation (6), in the computer, is provided. Each step is realized by the analyzer.

Hereinafter, as an analyzing method of the steel deformation processing of the embodiment, an order of analyzing the strain distribution when the hole expanding processing which is one type of the press forming is performed with respect to the steel sheet, by the finite element method, will be described.

Figure 37:
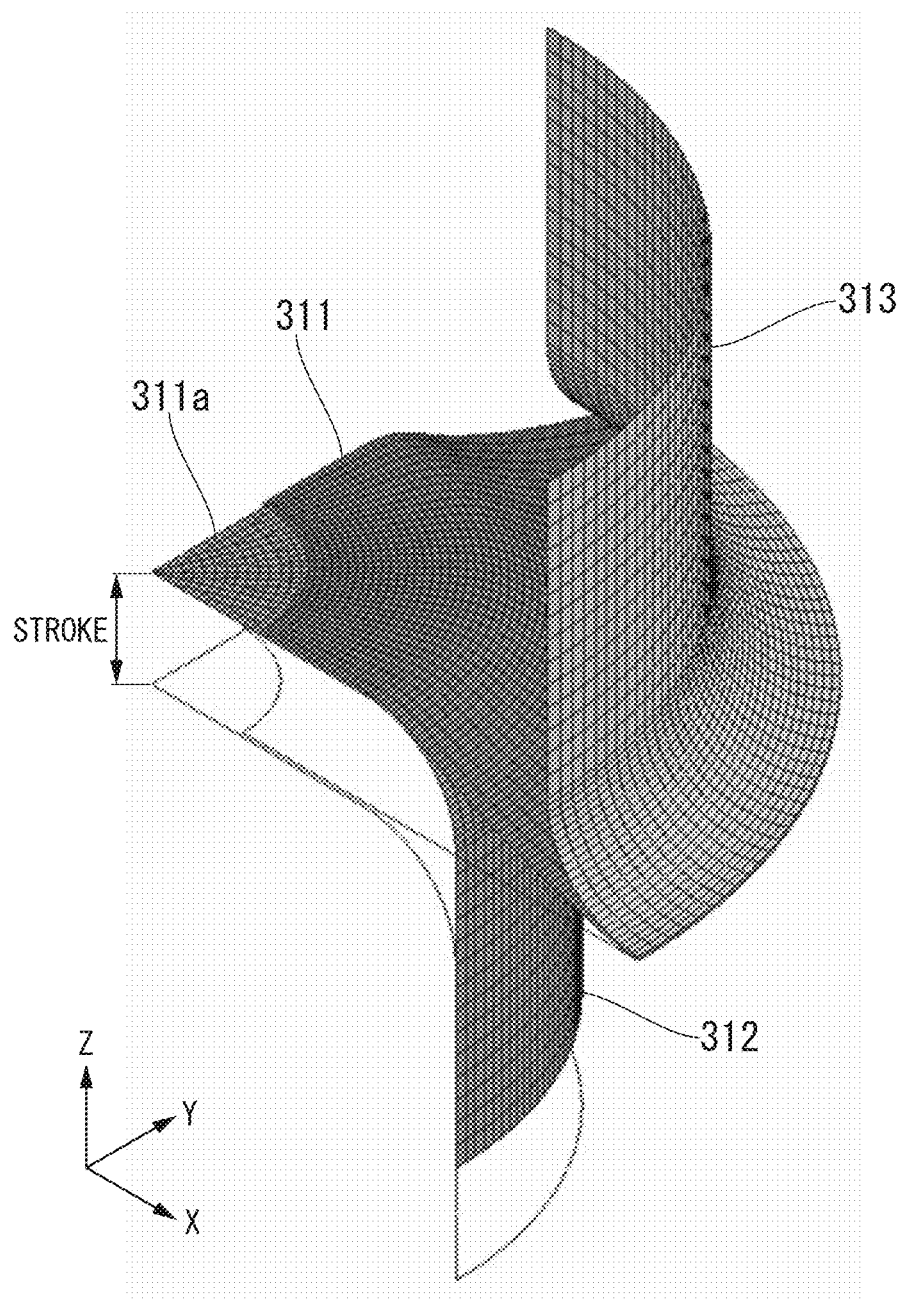
FIG. 37 is a partial perspective view illustrating a processing method of the cylindrical hole expanding processing.

First, a process of the hole expanding processing will be described with reference to FIG. 37. FIG. 37 is a perspective view after cutting out ¼ of the entire steel sheet, the punch, and the die. As illustrated in FIG. 37, a blank 311 (steel sheet) provided with a hole 311a is prepared, a punch 312 for expanding a hole is disposed below the blank 311, and a die 313 is disposed on the blank 311. In addition, by raising the punch 312, the hole expanding processing which widens the hole 311a provided in the blank 311 is performed.

A case where cracks are not generated at an edge part of the hole of the blank 311 after the hole expanding processing, is not considered as a forming defect, and a case where cracks are generated, is considered as a forming defect. When excessive stress is partially concentrated with respect to the edge part of the hole, a possibility of generation of cracks increases. Here, by the forming analysis which uses the finite element method, the distribution of the stress of the edge part of the hole of the blank 311 after the hole expanding processing is predicted.

Figure 36:
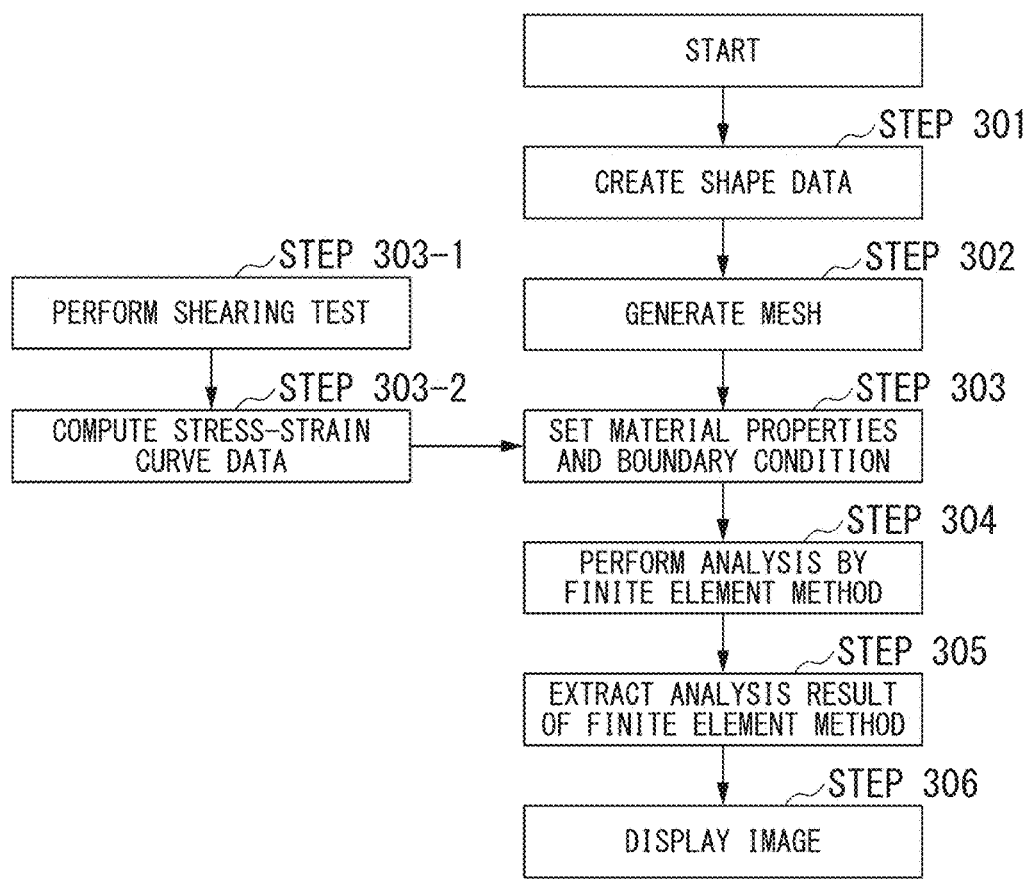
FIG. 36 is a flow view illustrating the evaluation method of the deformation processing of the steel according to the fourth embodiment of the present invention.

As illustrated in FIG. 36, first, in step 301, shape data of the steel sheet (blank) which is the analysis target is created.

Next, in step 302, a mesh is generated by dividing the shape data created in step 301 by the finite element. The generation of the mesh can use, for example, a mesh generation program included in an analysis package or the like of a commercially available finite element method. A shape of the finite element may be any of a triangle and a quadrangle. The size of the finite element may be appropriately set in accordance with the size, the shape, the thickness, and the boundary condition of the steel sheet which is the analysis target.

Next, in step 303, the material properties and the boundary condition of the steel sheet are set. In addition, in the step 303, K(MPa), a, b, c, and n* which are material parameters in the above-described equation (6) are input to the analyzer of the computer. Specific parameters vary in each type of steel sheet, but for example, is illustrated in the following table 1.

TABLE 1

| Type of steel | K(MPa) | a | n* | b | C |
|---|---|---|---|---|---|
| IF steel sheet | 480 | 0.0361 | 0.081 | 16.93 | 0.2363 |
| Steel sheet of 590 MPa | 982 | 0.0056 | 0.139 | 150.4 | 0.1731 |
| Steel sheet of 980 MPa | 1353 | 0.0001 | 0.063 | 3388 | 0.0067 |

The material properties are the sheet thickness or elastic modulus of the steel sheet which is the blank 311, and may use the physical properties of the steel sheet as it is. For example, in a case of the steel sheet in which the tensile strength is 1050 MPa, the yield strength is 730 MPa, and the sheet thickness is 1.6 mm is used, each of the physical properties is input.

In addition, the boundary conditions are a binding position, a load position, and a load weight of the blank 311 when the cylindrical hole expanding processing is performed with respect to the blank 311. When the cylindrical hole expanding processing is performed, the binding position may be a position at which the blank 311 is bound by the punch 312 and the die 313. In addition, in a case where the load is applied to the blank 311 by the cylindrical hole expanding processing, the load position may be a position at which the load is transmitted to the blank 311.

In addition, the material parameters, such as K(MPa), a, b, c, and n*, which are input in step 303, are used in the finite element analysis instead of the parameters of the work hardening law, such as the Swift equation of the related art. Each material parameter may be obtained in advance for each type of steel may be used. In addition, each material parameter may be obtained from the synthesized stress-strain curve data obtained by sequentially performing step 303-1 of performing the simple shearing test and step 303-2 of creating the synthesized stress-strain curve data based on the result of the simple shearing test.

Next, in step 304, the finite element analysis is performed based on the mesh, the material properties, and the boundary condition. For example, as analysis software, NASTRAN or ABAQUS which is a multi-purpose structure analysis finite element method code of a static implicit method, or LS-Dyna which is nonlinear dynamic analysis by an explicit method, can be used.

Figure 38A:
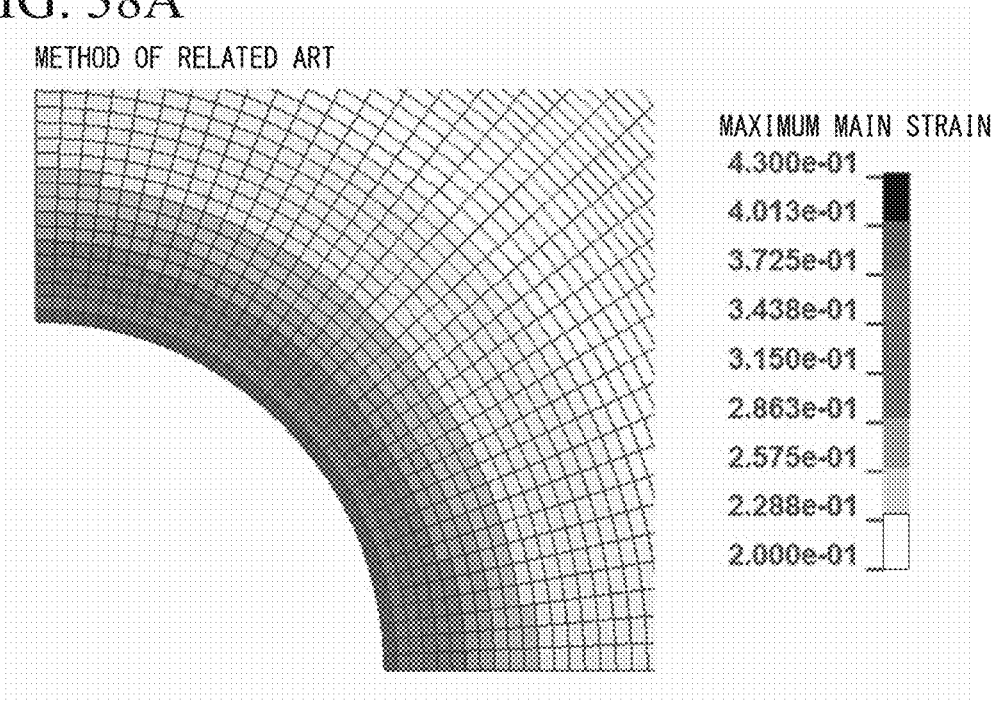
FIG. 38A is an outline view illustrating a result of performing analysis of the cylindrical hole expanding processing of the steel sheet based on the material parameter obtained by the Swift equation of the related art.
Figure 38B:
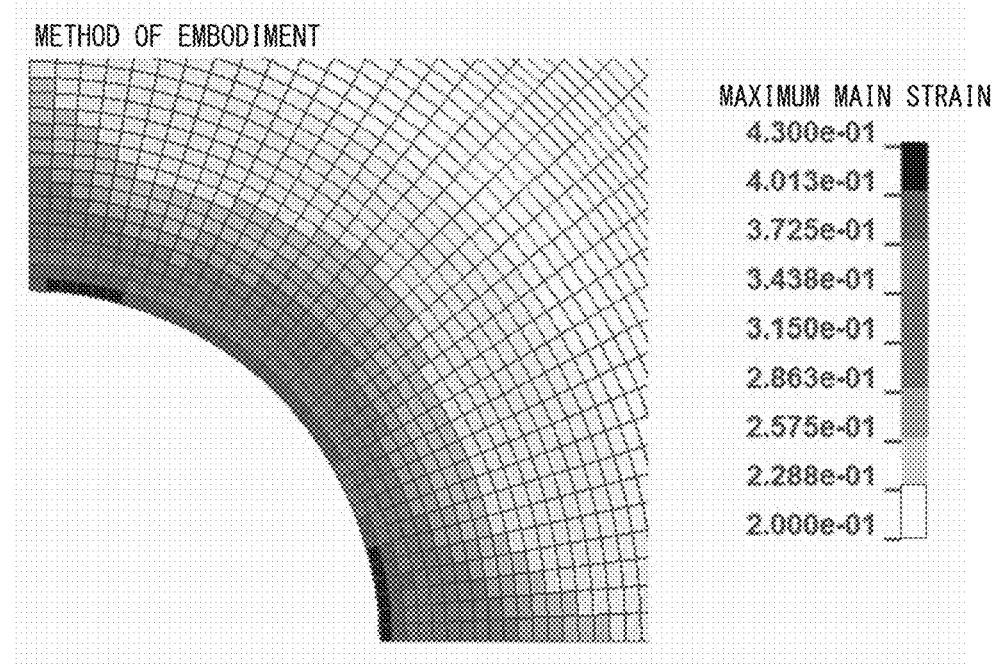
FIG. 38B is an outline view illustrating a result of performing analysis of the cylindrical hole expanding processing of the steel sheet based on the synthesized stress-strain curve data obtained by the evaluation method of the steel according to the third embodiment of the present invention.
Figure 39:
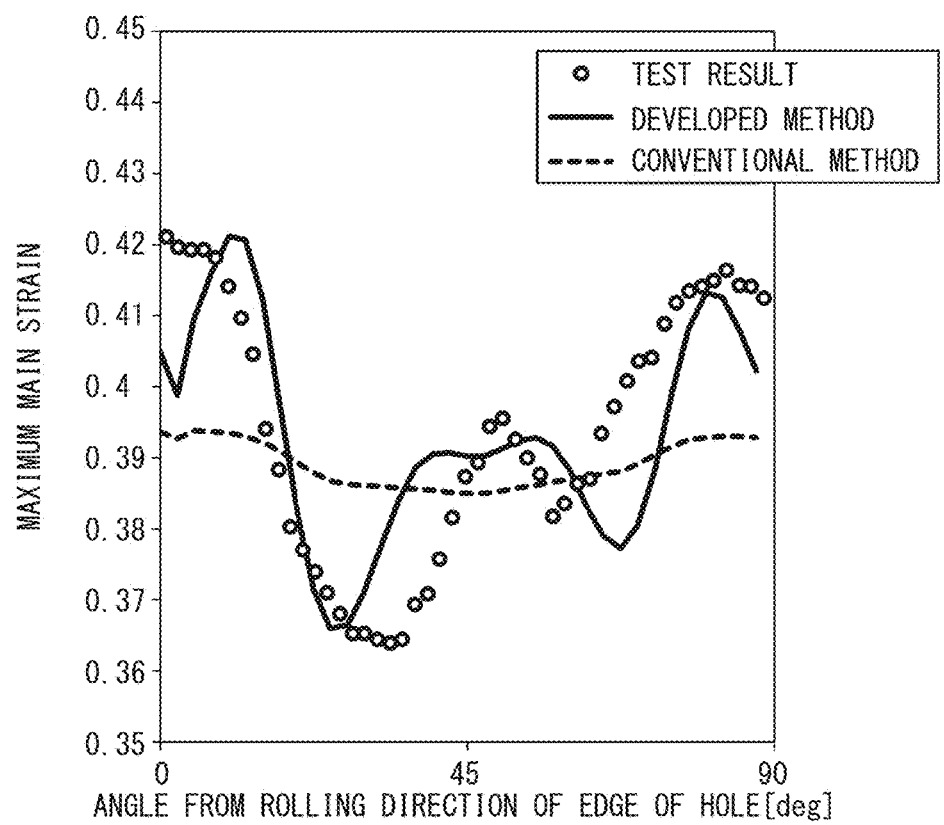
FIG. 39 is a graph illustrating a distribution of the maximum main strain amount at the edge of the hole after the cylindrical hole expanding processing of the steel sheet.

Next, in step 305, the result obtained in the finite element analysis is extracted. In addition, in step 306, the analysis result is output as a screen to the output device of the computer. In FIGS. 38A, 38B, and 39, an example of the analysis result is illustrated.

In FIGS. 38A and 38B, a cylindrical hole expanding analysis result of the steel sheet is illustrated. FIG. 38A is an outline view illustrating a result of performing the analysis of the cylindrical hole expanding processing of the steel sheet based on a material parameter obtained by the Swift equation of the related art. In addition, FIG. 38B is an outline view illustrating a result of performing the analysis of the cylindrical hole expanding processing of the steel sheet based on the synthesized stress-strain curve data obtained by the evaluation method of the steel according to the third embodiment of the present invention. FIGS. 38A and 38B illustrate the strain distribution when reaching a stroke amount by which cracks are generated by actually performing the hole expanding processing. In addition, in FIG. 39, the distribution of the maximum main strain amount at the edge of the hole after the cylindrical hole expanding processing of the steel sheet, is illustrated. A developed method of FIG. 39 is the result of the forming analysis of the embodiment which corresponds to that of FIG. 38B, and a conventional method of FIG. 39 is the result of the forming analysis of the related art which corresponds to that to FIG. 38A. In addition, the test result of FIG. 39 is the result obtained by actually performing the hole expanding processing.

As illustrated in FIG. 38A and 39, in the conventional method, the maximum strain amount at the part of the edge of the hole is approximately 0.39, and regardless of the angle from the rolling direction of the edge of the hole, the distribution of the strain amount is also relatively uniform. Therefore, in the conventional method, it is determined that the risk of generation of cracks are low. Meanwhile, as illustrated in FIGS. 38B and 39, in the evaluation method of the embodiment, the maximum strain amount at the part of the edge of the hole is approximately 0.42, and the strain is locally high. This tendency excellently matches the result obtained by actually performing the cylindrical hole expanding processing with respect to the steel sheet. Therefore, it is ascertained that the evaluation method of the deformation processing of the steel according to the embodiment can be performed as the forming analysis with higher accuracy compared to the related art.

According to the evaluation method of the deformation processing of the steel according to the embodiment, since the maximum strain distribution in a case where the deformation processing is performed with respect to steel is obtained by the finite element method by using the relational equation expressed by the above-described equation (6) as the relational approximation between the equivalent plastic stress and the plastic strain, it is possible to correctly obtain the maximum strain distribution in a case where the deformation processing is performed with respect to the steel material. For example, in a case where the press forming of the steel sheet is employed as the deformation processing, it is possible to correctly detect the generation of cracks of the steel sheet in the press forming.

Above, the present invention is described in detail based on the first embodiment to the sixth embodiment, but any of the above-described embodiments is merely a specified example for realizing the present invention, and the technical range of the present invention is not restrictively interpreted by the embodiments. For example, it is possible to appropriately employ the contents described in each embodiment to other embodiments.

As an analyzer which uses the synthesized stress-strain curve data, an analysis program of a commercially available finite element method may be used, an analyzer in a fracture prediction method in Japanese Unexamined Patent Application, First Publication No. 2007-232715 may be employed, an analyzer in a fracture prediction method in Japanese Unexamined Patent Application, First Publication No. 2007-285832 may be employed, and an analyzer in a bending fracture prediction method of a material in Japanese Unexamined Patent Application, First Publication No. 2012-33039 may be employed.

In the description above, the steel (that is, the steel sheet which is the plastic sheet) which is the plastic material is used, but as the plastic material, it is possible to use a metal material, such as aluminum or titanium, a glass fiber-reinforcing resin material, such as FRP or FRTP, and further, a composite material thereof.

Figure 40:
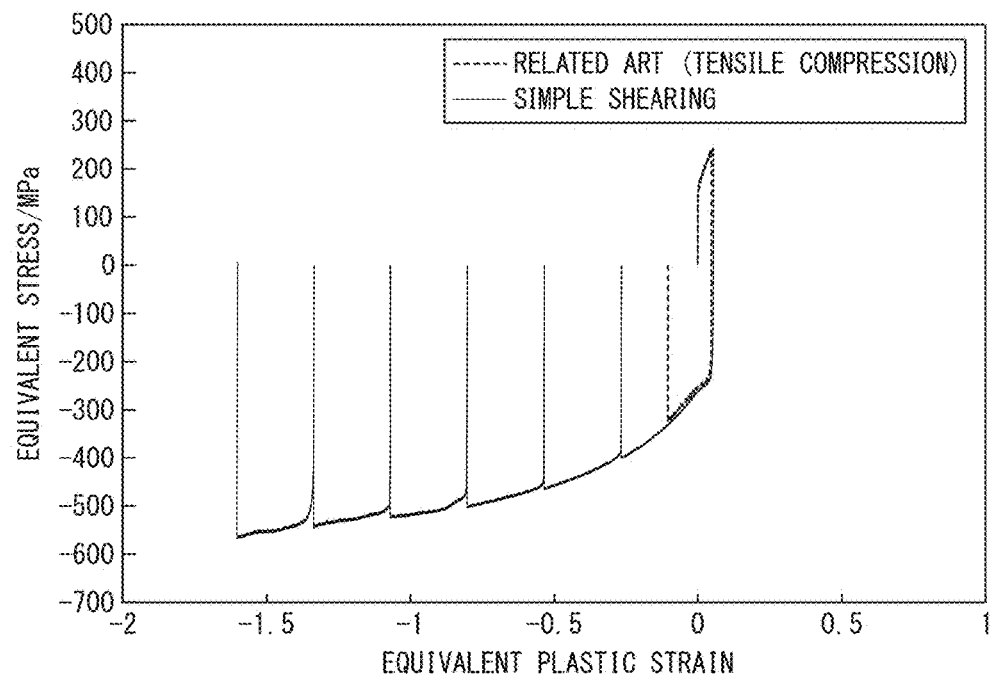
FIG. 40 is a graph illustrating the synthesized stress-strain curve data in a case where the application direction of the shear stress is reversed in the middle of the first shearing process.

In the description above, the plural pieces of partial stress-strain curve data are obtained when the direction in which the shear stress is loaded is considered as a constant direction in the shearing process, but as illustrated in FIG. 40, for example, the synthesized stress-strain curve data may be obtained by reversing the application direction of the shear stress in the middle of the first shearing process. In this case, since it is possible to obtain the synthesized stress-strain curve data when the inverse load is applied, it is possible to evaluate a Bauschinger effect which is a phenomenon of deterioration of the yield stress.

Figure 41:
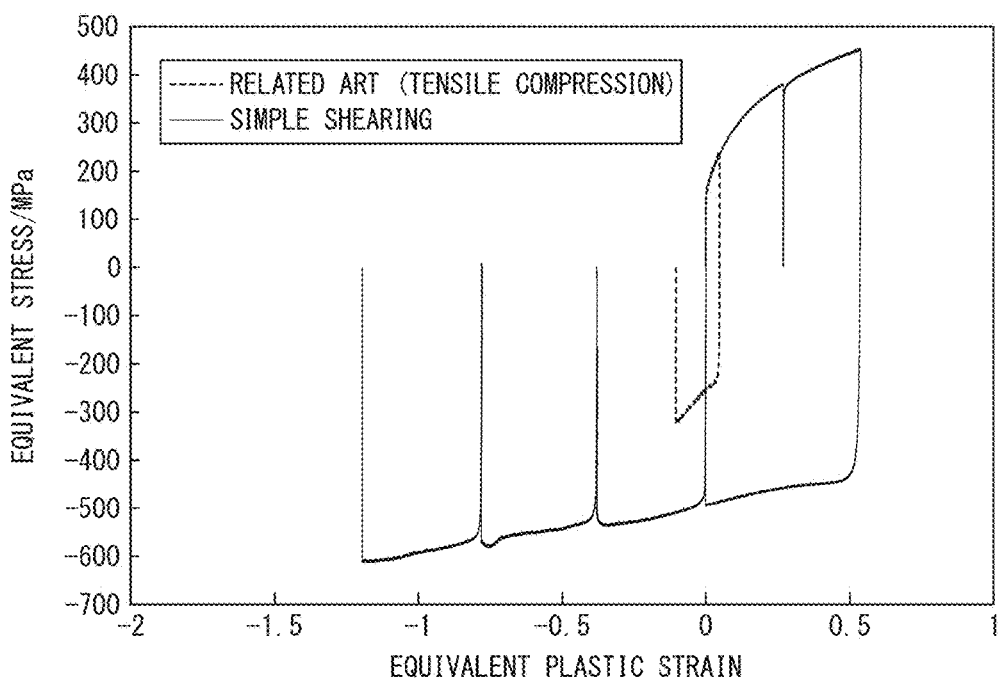
FIG. 41 is a graph illustrating rigidity stress-strain curve data in a case where the application direction of the shear stress is reversed in the third shearing process.

In addition, as illustrated in FIG. 41, for example, the synthesized stress-strain curve data may be obtained by reversing the application direction of the shear stress after the third shearing process. In this case, since it is also possible to obtain the synthesized stress-strain curve data when the inverse load is applied, it is possible to evaluate a Bauschinger effect which is a phenomenon of deterioration of the yield stress. In particular, since it is possible to reverse the load direction at the time when a desirable strain amount is loaded, it is possible to obtain the synthesized stress-strain curve data having higher practicability.

Furthermore, as illustrated in FIGS. 41 and 42, in a case where the plural pieces of partial stress-strain curve data are obtained by reversing the application direction of the shear stress, by approximating the partial stress-strain curve data based on the kinematic hardening law, such as a Lemaitre-Chaboche model or a Yoshida-Uemori model, it is possible to obtain a wider range of synthesized stress-strain curve data.

INDUSTRIAL APPLICABILITY

According to the present invention, it is possible to provide an evaluation method of a plastic material which can obtain highly accurate stress-strain curve data until reaching a strain region which exceeds uniform elongation, and an evaluation method of deformation processing of a plastic material which can perform forming analysis of deformation processing with high accuracy based on the stress-strain curve data obtained by the evaluation method of the plastic material.

BRIEF DESCRIPTION OF THE REFERENCE SYMBOLS 101, 201, 301 FIRST STEEL SHEET (FIRST PLASTIC SHEET)
101a, 201a, 301a ONE SIDE
101b, 201b, 301b THE OTHER SIDE
101c, 201c, 301c VIRTUAL SECTION
101d, 201d, 301d SHEARING DEFORMATION PART
101e, 201e, 301e SIDE (OUTER FORM PART)
102, 202 SECOND STEEL SHEET (SECOND PLASTIC SHEET)
203 THIRD STEEL SHEET (THIRD PLASTIC SHEET)

The invention claimed is:

1. An evaluation method of a plastically deformable material comprising:
a first shearing process of performing simple shearing deformation with respect to a first plastically deformable sheet by dividing the first plastically deformable sheet having a first strain amount, in a range which includes 0, into two regions by a virtual section perpendicular to a surface thereof, and by applying a shear stress to the first plastically deformable sheet so as to make relative positions of the two regions shifted along the virtual section be on the same surface;
a second shearing process of performing simple shearing deformation with respect to a second plastically deformable sheet by dividing the second plastically deformable sheet having a second strain amount which is different from the first strain amount, the second strain amount in a range including 0, into two regions by a virtual section perpendicular to a surface thereof, and by applying a shear stress to the second plastically deformable sheet so as to make relative positions of the two regions shifted along the virtual section be on the same surface;
a first partial stress-strain curve data obtaining process of obtaining first partial stress-strain curve data from a relationship between the shear stress applied to the first plastically deformable sheet in the first shearing process, and a total strain amount which is a sum of a shear strain amount which is applied to the first plastically deformable sheet in the first shearing process and the first strain amount, by measuring the shear stress and the shear strain which are applied to the first plastically deformable sheet in the first shearing process;

a second partial stress-strain curve data obtaining process of obtaining second partial stress-strain curve data from a relationship between the shear stress applied to the second plastically deformable sheet in the second shearing process, and a total strain amount which is a sum of a shear strain amount which is applied to the second plastically deformable sheet in the second shearing process and the second strain amount, by measuring the shear stress and the shear strain which are applied to the second plastically deformable sheet in the second shearing process;

a synthesized stress-strain curve data obtaining process of obtaining synthesized stress-strain curve data based on the first partial stress-strain curve data and the second partial stress-strain curve data; and a process of outputting the synthesized stress-strain curve data to a display device.

2. The evaluation method of a plastically deformable material according to claim 1, further comprising:

an outer form removing process of obtaining the second plastically deformable sheet by removing an outer form part of the first plastically deformable sheet after unloading the shear stress applied in the first shearing process.

3. The evaluation method of a plastically deformable material according to claim 2, wherein, in the outer form removing process, the outer form part is removed across the two regions of the first plastically deformable sheet along the surface direction perpendicularly intersecting the virtual section and a flat surface of the first plastically deformable sheet.

4. The evaluation method of a plastically deformable material according to claim 1, wherein the first plastically deformable sheet and the second plastically deformable sheet are individual plastically deformable sheets different from each other.

5. The evaluation method of a plastically deformable material according to claim 4, wherein the second strain amount is greater than the first strain amount, and is equal to or less than the strain amount applied to the first plastically deformable material in the first shearing process.

6. The evaluation method of a plastically deformable material according to claim 4, wherein, in the synthesized stress-strain curve data obtaining process, the synthesized stress-strain curve data is obtained by combining the curve data of a strain region other than a part which receives the influence of a cross-over effect from the first partial stress-strain curve data and the second partial stress-strain curve data.

7. The evaluation method of a plastically deformable material according to claim 4, further comprising:

an outer form removing process of obtaining a third plastically deformable sheet having a third strain amount different from the first strain amount and the second strain amount by removing an outer form part formed by the simple shearing deformation in the first plastically deformable sheet;

a third shearing process of performing simple shearing deformation with respect to the third plastically deformable sheet by dividing the third plastically deformable sheet into two regions by a virtual section perpendicular to the surface thereof, and by applying a shear stress to the third plastically deformable sheet so as to make relative positions of the two regions shifted along the virtual section be on the same surface; and a third partial stress-strain curve data obtaining process of obtaining third partial stress-strain curve data from a relationship between the shear stress applied to the third plastically deformable sheet in the third shearing process, and a total strain amount which is a sum of a shear strain amount which is applied to the third plastically deformable sheet in the third shearing process and the third strain amount, by measuring the shear stress and the shear strain which are applied to the third plastically deformable sheet in the third shearing process, wherein, in the synthesized stress-strain curve data obtaining process, the synthesized stress-strain curve data is obtained based on the first partial stress-strain curve data, the second partial stress-strain curve data, and the third partial stress-strain curve data.

8. The evaluation method of a plastically deformable material according to claim 1, wherein, in the synthesized stress-strain curve data obtaining process, the synthesized stress-strain curve data is obtained by approximating the first partial stress-strain curve data and the second partial stress-strain curve data based on a work hardening law.

9. The evaluation method of a plastically deformable material according to claim 1, wherein, in the synthesized stress-strain curve data obtaining process, the synthesized stress-strain curve data is obtained by approximating the first partial stress-strain curve data and the second partial stress-strain curve data by a relational equation expressed by the following equation (1), $$\sigma = K(\varepsilon^p + a)^m \tag{1}$$

$$m = n^* + 1/\{b(\varepsilon^p + c)\} \tag{2}$$

here, in equation (1), $\sigma$ is an equivalent stress, K (MPa) and a are material factors of the plastically deformable material, $\varepsilon^p$ is an equivalent plastic strain, and m is as illustrated in the above-described equation (2), and in equation (2), $n^*$ is a convergence value of a work hardening coefficient, b is a parameter indicating the rate of convergence of the work hardening coefficient, and c is a parameter indicating the rate of development of the work hardening coefficient.

10. The evaluation method of a plastically deformable material according to claim 1, wherein the application direction of the shear stress in the first shearing process and the application direction of the shear stress in the second shearing process are opposite to each other.

11. The evaluation method of a plastically deformable material according to claim 1, wherein, in the first shearing process, the application direction of the shear stress is reversed in the middle.

12. The evaluation method of a plastically deformable material according to claim 10, wherein, in the synthesized stress-strain curve data obtaining process, the synthesized stress-strain curve data is obtained by approximating the first partial stress-strain curve data and the second partial stress-strain curve data based on a kinematic hardening law.

13. The evaluation method of a plastically deformable material according to claim 1, wherein the first plastically deformable sheet and the second plastically deformable sheet have a shape of a rectangular flat surface.

14. The evaluation method of a plastically deformable material according to claim 1,
wherein, in the first shearing process and the second shearing process, the largest amount of change in the sheet thickness of the first plastically deformable sheet and the second plastically deformable sheet is equal to or less than 1% of the sheet thickness.

15. The evaluation method of a plastically deformable material according to claim 1,
wherein the shear strain applied in each of the first shearing process and the second shearing process, is in a range of 0.4 to 1.2.

16. The evaluation method of a plastically deformable material according to claim 1,
wherein the first plastically deformable sheet and the second plastically deformable sheet are steel sheets.

17. An evaluation method of deformation processing of a plastically deformable material,
wherein a computer provided with an analyzer which performs forming analysis of deformation processing of the plastically deformable material by a finite element method is used,
wherein the synthesized stress-strain curve data obtained by the evaluation method of the plastically deformable material according to claim 1 is input to the analyzer of the computer, and
wherein the analyzer is operated by the computer.

18. The evaluation method of deformation processing of a plastically deformable material according to claim 17,
wherein the forming analysis obtains at least one of a strain distribution, the maximum strain, and a forming load of the plastically deformable material in a case where the deformation processing is performed with respect to the plastically deformable material.

19. An evaluation method of a plastically deformable material comprising:
a first shearing process of performing simple shearing deformation with respect to a first plastically deformable sheet by dividing the first plastically deformable sheet having a first strain amount, in a range which includes 0, into two regions by a virtual section perpendicular to a surface thereof, and by applying shear stress to the first plastically deformable sheet so as to make relative positions of the two regions shifted along the virtual section be on the same surface;

a first partial stress-strain curve data obtaining process of obtaining first partial stress-strain curve data from a relationship between the shear stress applied to the first plastically deformable sheet in the first shearing process, and a total strain amount which is a sum of a shear strain amount which is applied to the first plastically deformable sheet in the first shearing process and the first strain amount, by measuring the shear stress and the shear strain which are applied to the first plastically deformable sheet in the first shearing process;

a synthesized stress-strain curve data obtaining process of obtaining synthesized stress-strain curve data by approximating the first partial stress-strain curve data by a relational equation expressed by the following equation (3); and a process of outputting the synthesized stress-strain curve data to a display device:

$$\sigma = K(\varepsilon^p + a)_m \tag{3}$$

$$m = n^* + 1/\{b(\varepsilon^p + c)\} \tag{4}$$

here, in equation (3), $\sigma$ is an equivalent stress, K (MPa) and a are material factors of the plastically deformable material, $\varepsilon^p$ is an equivalent plastic strain, and m is as illustrated in the above-described equation (4), and in equation (4), n* is a convergence value of a work hardening coefficient, b is a parameter indicating the rate of convergence of the work hardening coefficient, and c is a parameter indicating the rate of development of the work hardening coefficient.

20. An evaluation method of deformation processing of a plastically deformable material,
wherein a computer provided with an analyzer which performs forming analysis of deformation processing of the plastically deformable material by a finite element method is used,
wherein the synthesized stress-strain curve data obtained by the evaluation method of the plastically deformable material according to claim 19 is input to the analyzer of the computer, and
wherein the analyzer is operated by the computer.

21. The evaluation method of deformation processing of a plastically deformable material according to claim 20,
wherein the forming analysis obtains at least one of a strain distribution, the maximum strain, and a forming load of the plastically deformable material in a case where the deformation processing is performed with respect to the plastically deformable material.

* * * * *